U\S011150236B2

United States Patent
Dewilde et al.

(10) Patent No.: US 11,150,236 B2
(45) Date of Patent: Oct. 19, 2021

(54) MULTI-WELL QUARTZ CRYSTAL MICROBALANCE MASS AND VISCOELASTIC SENSOR

(71) Applicant: UNIVERSITY OF MASSACHUSETTS, Boston, MA (US)

(72) Inventors: Abiche H. Dewilde, Tewksbury, MA (US); Berk Akinci, Tewksbury, MA (US); Joel M. Therrien, Westford, MA (US); Kenneth A. Marx, Francestown, NH (US); Susan J. Braunhut, Wellesley, MA (US)

(73) Assignee: University of Massachusetts, Boston, MA (US)

( * ) Notice: Subject to any disclaimer, the term of this patent is extended or adjusted under 35 U.S.C. 154(b) by 620 days.

(21) Appl. No.: 15/436,136

(22) Filed: Feb. 17, 2017

(65) Prior Publication Data

US 2017/0241982 A1    Aug. 24, 2017

Related U.S. Application Data

(60) Provisional application No. 62/297,374, filed on Feb. 19, 2016.

(51) Int. Cl.
*G01N 33/50*    (2006.01)
*G01N 29/02*    (2006.01)
*G01N 29/22*    (2006.01)

(52) U.S. Cl.
CPC ....... *G01N 33/5014* (2013.01); *G01N 29/022* (2013.01); *G01N 29/222* (2013.01);
(Continued)

(58) Field of Classification Search
CPC ......... G01N 33/5014; G01N 2291/014; G01N 2291/0255; G01N 29/222;
(Continued)

(56) References Cited

U.S. PATENT DOCUMENTS

| 2006/0109630 | A1* | 5/2006 | Colgan | .................. H01L 23/42 |
| | | | | 361/718 |
| 2015/0094914 | A1* | 4/2015 | Abreu | ................ B60H 1/00742 |
| | | | | 701/41 |
| 2017/0322171 | A1* | 11/2017 | Bather | ............... G01N 27/4143 |

FOREIGN PATENT DOCUMENTS

WO    WO 2004 040261 A2    5/2004

OTHER PUBLICATIONS

Ping Kao, et al, "Fabrication and performance characteristics of high-frequency micromachined bulk acoustic wave quartz resonator arrays", Measurement Science and Technology, IOP, Bristol, GB, vol. 20, No. 12, Dec. 1, 2009, pp. 124007 (9pp).

(Continued)

*Primary Examiner* — Rebecca M Fritchman
(74) *Attorney, Agent, or Firm* — Armis IP Law, LLC

(57) ABSTRACT

In an embodiment, a system includes a plurality of sensor devices contained in a plurality of wells contained in a well-plate assembly. The sensor devices are used in a plurality of oscillators. Each oscillator generates a frequency and a resistance based on a quality of living biological cells contained in a corresponding well. The quality may include, for example, surface coupled mass, density, viscosity, and/or viscoelasticity of the living biological cells. The system also includes logic for measuring a resonant frequency and motional resistance associated with each sensor device and logic for processing the measured resonant frequency and motional resistance. Moreover, the system includes logic for displaying one or more graphs showing one or more characteristics of the living biological cells contained in the wells.

18 Claims, 21 Drawing Sheets

(52) U.S. Cl.
CPC ............... *G01N 2291/014* (2013.01); *G01N 2291/0255* (2013.01); *G01N 2291/02809* (2013.01); *G01N 2291/02818* (2013.01)

(58) Field of Classification Search
CPC ....... G01N 2291/02818; G01N 29/022; G01N 2291/02809
See application file for complete search history.

(56) References Cited

OTHER PUBLICATIONS

International Search Report, PCT/US2017/018391, dated Jun. 21, 2017, pp. 5.

\* cited by examiner

MULTI-WELL QUARTZ CRYSTAL MICROBALANCE MASS AND VISCOELASTIC SENSOR

RELATED APPLICATIONS

This application claims priority to and the benefit of U.S. Provisional Patent Application No. 62/297,374, titled "MULTI-WELL QUARTZ CRYSTAL MICROBALANCE MASS AND VISCOELASTIC SENSOR", filed on Feb. 19, 2016. The above-identified application is incorporated herein by reference as though fully set forth herein.

BRIEF DESCRIPTION OF THE DRAWINGS

The accompanying drawings, which are incorporated in and constitute a part of this specification, illustrate one or more embodiments described herein and, together with the description, explain these embodiments. In the drawings.

DETAILED DESCRIPTION

Figure 1:
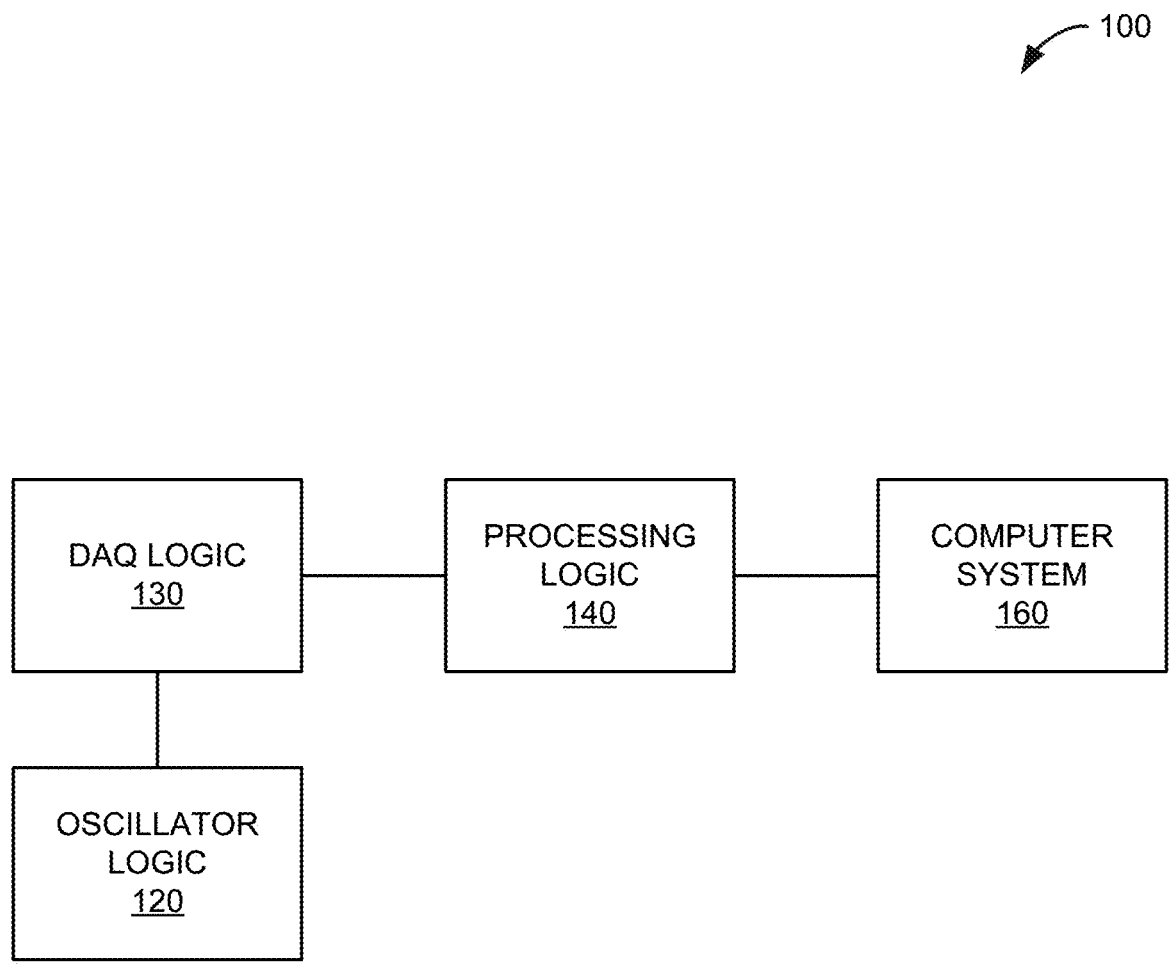
FIG. 1 illustrates an example of a data acquisition (DAQ) system that may implement techniques described herein.

The following detailed description refers to the accompanying drawings. The same reference numbers in different drawings may identify the same or similar elements. Also, the following detailed description does not limit the invention.

Quartz crystal microbalance (QCM) may involve, for example, a weight measuring technique that may use a thin slice of crystal to measure weight. The crystal may be part of an oscillator that may apply an electrical field to the crystal to cause the crystal to physically move (e.g., oscillate) back and forth based on the electric field. If mass is added to or removed from the crystal while it is moving, its rate of movement may change proportionately. This change may manifest as a change of frequency of the oscillator.

A system may employ QCM techniques to measure a deposition of peptides, substrates, and/or ligands as they interact with antibodies, enzymes, and/or receptors in a solution. The system may employ, for example, a single well that may be used to hold an experiment containing the deposition and the solution. A design of the system may be such that experiments conducted using the system may have to be performed outside a controlled environment that may be provided by, for example, an incubator.

One disadvantage associated with such a system is that operating outside a controlled environment may cause results produced by the system to vary due to outside environmental influences. Another disadvantage with such a system is that since it employs a single-well, the system may not be capable of simultaneously performing an experiment on a control group and an experimental group in separate wells.

Techniques described herein may be used to obviate the above-described disadvantages. A system that employs techniques described herein may include a multi-well system that may be used in a controlled environment such as, for example, an incubator. The multi-well system may include a plurality of wells that may be used to conduct multiple experiments simultaneously. Thus, the multi-well system may, for example, accommodate performing an experiment simultaneously in multiple wells that are contained in a controlled environment. The multiple wells may include a well that contains sample material (e.g., living biological cells) from an experimental group and another well that contains sample material from a control group.

Techniques described herein may use QCM techniques to detect a change in mass of a material bound to a crystal's surface. In addition, techniques described herein may be used to identify qualities of the material, such as, for example, a viscosity and/or density of the material.

For example, if material on the crystal has a liquid or gel-like property, while the material is set into motion, it may dissipate the crystal's energy. Techniques described herein can identify various qualities associated with the material by measuring this dissipation. The identified qualities may include, for example, viscoelastic properties and/or density of the material bound to the crystal.

Applications of techniques described herein may include measuring a deposition of materials such as, peptides, substrates, and/or ligands, as they bind to a crystal. In addition, interaction of other materials, such as, antibodies, enzymes and/or receptors, with the materials bound to the crystal may be measured. Here, the interaction may be measured based on, for example, frequency changes to the crystal caused by the interaction.

Techniques described herein may involve using sensor devices (e.g., QCM crystals) with adherent cells (e.g., living biological whole cells), which can bind to the sensor device's surface. The techniques may be used to measure, for example, how the cells attach. In addition, techniques described herein may be used to determine whether cells undergo characteristic motions by, for example, detecting patterns in frequency and resistance of the sensor devices. Moreover, techniques described herein may be used to determine a perturbation of well-organized subcellular structures inside cells. For example, techniques described herein may be used to identify a perturbation of subcellular organelles due to an agent. This determination may be made, for example, by observing frequencies and resistances associated with the sensor devices.

After cells are bound stably to a sensor device, the cells may be used as sensitive broad-spectrum biosensors that can be rationally perturbed by materials, such as, growth factors, toxins, drugs, differentiating agents and/or other bioactive agents. Their response can be precisely monitored by parameter changes in a sensor device that may result from alterations in the biomechanics of cells as they react to different stimuli.

In an embodiment, a sensor device may employ a QCM crystal that when put within an alternating electric field, a specific crystalline cut of the QCM crystal may physically oscillate at a high frequency (e.g., 10 megahertz (MHz)), and maintain this precise rate of oscillation. If mass as little as, for example, one nanogram (ng) couples to the QCM crystal, an oscillating frequency of the crystal may change (e.g., decrease) in a highly-correlated fashion. This property may allow for a detection of additional nanogram masses to the QCM crystal's surface. If the deposition of mass ceases, the oscillation frequency of the QCM crystal may stop changing. If coupled mass is degraded or uncoupled thereby causing, for example, loss of mass attached to the QCM crystal, the oscillating frequency of the QCM crystal may also change (e.g., increase) in a highly-correlated fashion. Techniques described herein may be used to identify and/or monitor these properties.

For example, if a known quantity of a substrate is added to a surface of an oscillating QCM crystal, this may result in a change (e.g., decrease) in oscillation frequency ($\Delta f$). After substrate deposition saturates, $\Delta f$ may level off to a new, stable lower oscillation rate. If an appropriate agent is added to the QCM crystal that can degrade that specific substrate on the QCM crystal's surface and the resulting product does not bind to the surface, it may cause a measurable loss of mass. Techniques described herein may be used to monitor a rate and removal of mass caused by the substrate. This monitoring may be performed, for example, in real-time. After living biological cells are added to an operating QCM crystal, increased mass deposition and cell attachment to the QCM crystal can also be detected using techniques described herein.

A quality of an attached mass (e.g., living biological cells) that may be measured using techniques described herein may include elasticity or deformability of a protein or cell on the surface of a sensor device. The "motional resistance" ($R_m$) of the sensor device (also known as "dissipation") may quantify a dampening of the system and can provide viscoelastic information of bound materials based on a change in $R_m$ ($\Delta R$).

These combined measures (i.e., $\Delta f$ and $\Delta R$) can be used to examine how cells attach, a strength and kinetics of attachment, their aggregated attachment (motility), stability, and/or degree of structural complexity within a cell (cytoskeleton). Even perturbation of a single type of subcellular organelle, e.g., the mitochondria, may be detected in living biological cells bound to the sensor device using techniques described herein. The combined measures may be used to measure a cell's mass distribution and/or the cell's viscoelastic properties that may be created by a manner and strength of cell attachment to the sensor device. Moreover, the combined measures may be used to measure an organization, number, and/or type of molecularly linked subcellular organelles and cytoskeletal elements within cells attached to the sensor device.

Embodiments of systems designed for use with living biological cells will be described further below. In an embodiment, a system includes an oscillator circuit and a sensor device. The sensor device includes a wafer of AT cut quartz crystal. Metal (e.g., gold) electrodes are placed on both sides of the quartz crystal, with one side functioning as the sensing area. The metal electrodes produce an alternating electric field, driving the quartz crystal to oscillate, for example, at a constant resonant frequency of 10 Mhz.

An increase of bound elastic mass on the (dry) quartz crystal surface may cause the crystal to change its resonant oscillation frequency. This change may be used to quantify, with, for example, nanogram sensitivity, an amount of mass added to the crystal surface. For energy-dissipating bound masses on the crystal surface (e.g., living biological cells), the change in crystal frequency may reflect both bound mass magnitude and viscoelastic properties. Here, for example, cellular attachment sensor device can result in a significant crystal frequency shift. An $R_m$ measurement of a sensor device may be sensitive to, for example, cell density and cell-to-cell interactions, the cell environment and to cellular changes due to biologically active species such as, drugs, signal transduction effectors, and so on, causing effects in, for example, both $\Delta f$ and $\Delta R$.

Techniques described herein may be used, for example, as a platform to streamline a drug research process. Techniques described here may be used to quantify cell-based research with adherent live cells in culture over multiple days—for pre-discovery, target identification and/or validation phases of drug discovery. Techniques described herein may be applied, for example, in drug discovery where a target and/or toxicity may be unknown, or in drug development where off target toxicity may be discovered. Techniques described herein may be used to generate quantitative results faster than existing practices with improved outcomes. Techniques described herein may be used in pharmaceutical research to validate research performed during a drug's discovery and/or development phase. Here, techniques described herein may be used to identify, for example, a mechanism of action and/or toxicity of the drug.

Techniques described herein may have uses in, for example, phenotypic cell research, applications in central nervous diseases (CNS), immunotherapy, companion diagnostics, and/or personalized medicine platforms. By employing, for example, a unique whole cell system, techniques described herein may be used to simulate multiple cell situations on a single plate and monitor the response in real time to mimic the interactions of interest for immuno-oncology, autoimmunity and inflammation targets.

Techniques described herein may provide organ simulation testing across organ cell lines, disease-cells, and/or immune cells. Techniques described herein may be used to produce real-time data that may enable rapid determination of mechanism of action. Techniques described herein may be used to assay, for example, different cell types of an organ in order to perform organ panel testing. This can then expand to test the panels of multiple organs thereby allowing, for example, human system simulation. Techniques described herein may be used, for example, to help determine if toxicity will be developed in the heart, lung, liver and/or kidney tissue and determine if a drug has specificity for an organ disease cell type, while sparing healthy cells.

FIG. 1 illustrates a block diagram of an example of a data acquisition (DAQ) system 100 that may be used with techniques described herein. The DAQ system 100 may be used to measure, for example, a quality associated of a material such as, for example, living biological cells. The quality of the material may include, for example, surface coupled mass, density, viscosity, and/or viscoelasticity of the material although other characteristics of the material may be measured.

Referring now to FIG. 1, system 100 may include several components such as, for example, oscillator logic 120, DAQ logic 130, processing logic 140, and computer system 160.

Oscillator logic 120 may include logic (e.g., electronic circuitry) that implements a plurality of oscillators (e.g., lever oscillators). The oscillators may produce, for example, data that reflect a quality of biological cells. Oscillator logic 120 may also include logic that transfers the data to the DAQ logic 130.

More specifically, oscillator logic 120 may include a plurality of sensor devices that may sense the quality of biological cells that may be contained in a plurality of wells. Each sensor device may be associated with one or more characteristics (e.g., resonant frequency, motional resistance) that may reflect a sensed quality of the cells. Sensing may include varying one or more of these characteristics in response to the quality of the biological cells.

For example, oscillator logic 120 may include a plurality of wells. Each well may contain a QCM crystal that senses a quality of contained living biological cells also contained in the well. Sensing may include, for example, varying a resonant frequency and/or motional resistance of the QCM crystal in response to the quality of the cells.

Oscillator logic 120 may include logic that may measure characteristics associated with the sensor devices. Oscillator logic 120 may also include logic that may produce data that may represent the measured characteristics. The data may be provided to the processing logic 140 (e.g., via the DAQ logic 130) which may process the data, accordingly.

The DAQ logic 130 may include logic that, for example, implements one or more modified reciprocal frequency counters. Here, each modified reciprocal frequency counter may be similar to a reciprocal frequency counter in that it counts a known internal time-base (clock) signal between events on a measured unknown external signal, but may be modified in that it does not synchronize to the unknown signal.

The modified reciprocal frequency counters may measure frequencies of the plurality of lever oscillators contained in oscillator logic 120. These frequencies may be measured concurrently, thus, enabling sample periods to be kept consistent across all the oscillators.

Events counted by the modified reciprocal frequency counter may include a rising edge of the oscillator output signal. In an embodiment, the rising edge is sampled by frequency counter logic at 400 million samples-per-second (MSps) hence each edge is detected with 2.5 nanosecond (ns) resolution. At 1 measurement-sample-per-second, this translates to frequency resolution of approximately 0.025 Hz with a 10 MHz input.

The frequency counters may be designed to leave no edge behind. This may enable making measurements more often than 1-per-second (e.g., 1000 per second) without sacrificing a resolution of the measurement. Enough information may be retained in a measurement to reconstruct a more precise measurement attainable by the slower sample rate.

The DAQ logic 130 may also include, for example, rising-edge sampling logic. The sampling logic may be configured to act as a "deserializer" (i.e., a serial-to-parallel converter). The deserializer may run faster than other logic contained in the DAQ logic 130. Edges may be found as a pattern in the parallelized input by slower logic contained in the DAQ logic 130. This technique may allow use of widely-available serialize-deserialize (Ser-Des) blocks or double data rate (DDR) blocks in programmable logic devices such as, for example, complex programmable logic devices (CPLDs) and field programmable gate arrays (FP-GAs). The Ser-Des blocks may routinely run at up to, for example, five gigasamples-per-second (GSps) (i.e., 5000 MSps). DDR blocks may run up to, for example, 1.6 GSps (i.e., 1600 MSps).

The DAQ logic 130 may include a CPLD that may acquire (e.g., receive) frequency data produced by the oscillator logic 120 and keep time for the system 100. In an embodiment, the CPLD includes sample timers, modified reciprocal frequency counters, a tagged data first-in-first-out (FIFO) memory, a diagnostic FIFO memory, and a serial peripheral interface (SPI). The SPI interface may include a 4-wire serial interface that may allow configuration, run/stop control, and data fetching.

The processing logic 140 may include a processor (e.g., microprocessor) that may be configured to, for example, process data produced by the oscillator logic 120 and the DAQ logic 130 and store the data in a database (e.g., a MySQL-based database) contained in processing logic 140. The data may include, for example, frequency data produced by the DAQ logic 130, automatic gain control (AGC) status information produced by the oscillator logic 120, and/or environmental data. The environmental data may be produced by environmental sensors that may measure various environmental conditions associated with a multi-well assembly (described further below). These environmental conditions may include, for example, temperature, humidity, pressure, and/or acceleration. It should be noted that in other embodiments, the database may reside outside of processing logic 140. For example, the database may be contained on a system that may be accessible to processing logic 140 via the Internet (e.g., a cloud server).

As noted above, the processing logic 140 may include a microprocessor. An example, of a microprocessor that may be used is the Raspberry Pi processor available from the Raspberry Pi Foundation, Caldecote, Cambridgeshire, United Kingdom. The processor may implement a database server and an operating system. The database server may maintain and provide access to the database contained in processing logic 140. An example of a database server that may be used is the MySQL Server available from Oracle Corporation, Redwood Shores, Calif. The operating system may control an operation of software that is executed by processing logic 140. An example of an operating system that may be used is the Debian Linux operating system, available from Software in the Public Interest, Incorporated, Indianapolis, Ind.

Processing logic 140 may also include a storage device. An example of a storage device that may be used includes a Secure Digital Card. The database and applications executed by processing logic 140 may be stored on the data storage device. Note that the database and/or applications may be stored on other media, and/or on a device that is not contained in processing logic 140.

Processing logic 140 may include provisions for performing DAQ processing. DAQ processing may include translating data stored in the database and controlling an acquisition of data from the DAQ logic 130 and/or oscillator logic 120. Translating the data may be performed by logic that may provide, for example, a MySQL-to-JavaScript-object-notation translation. Controlling acquisition of the data may be performed, for example, using scripts implemented using the PHP (PHP hypertext preprocessor) programming language.

Processing logic 140 may implement, for example, a web server to provide a user-friendly interface to processing logic 140. The web server may contain provisions for serving information (e.g., translated data) to the computer system 160. The information may be provided to the computer system in response to requests issued by a web browser that may be contained in the computer system 160.

The computer system 160 may be for example, a personal computer, tablet, phone, or some other type of computer system. Computer system 160 may include a processor that executes an operating system and/or applications. The applications may include a web browser which may exchange information with processing logic 140. Applications executed by computer system 160 may execute a programming and/or markup language which may provide a user interface. Examples of programming and/or markup languages that may be used include JavaScript, hypertext markup language (HTML), extensible markup language (XML), and/or some other programming and/or markup language. A user interface provided by the applications may include provisions for providing a real-time visualization of collected data as well as provisions for controlling acquisition/processing of data by, for example, by various components in system 100.

Figure 2A:
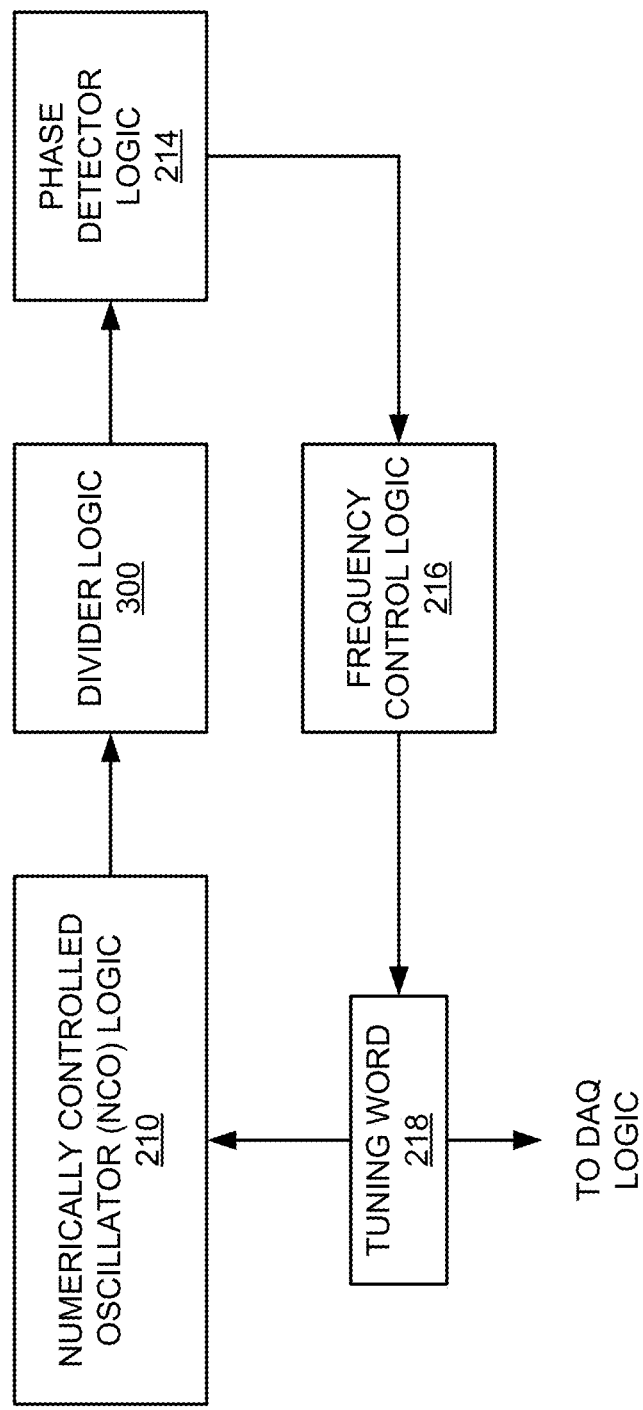
FIGS. 2A-B illustrate example block diagrams of embodiments of oscillator logic.
Figure 2B:
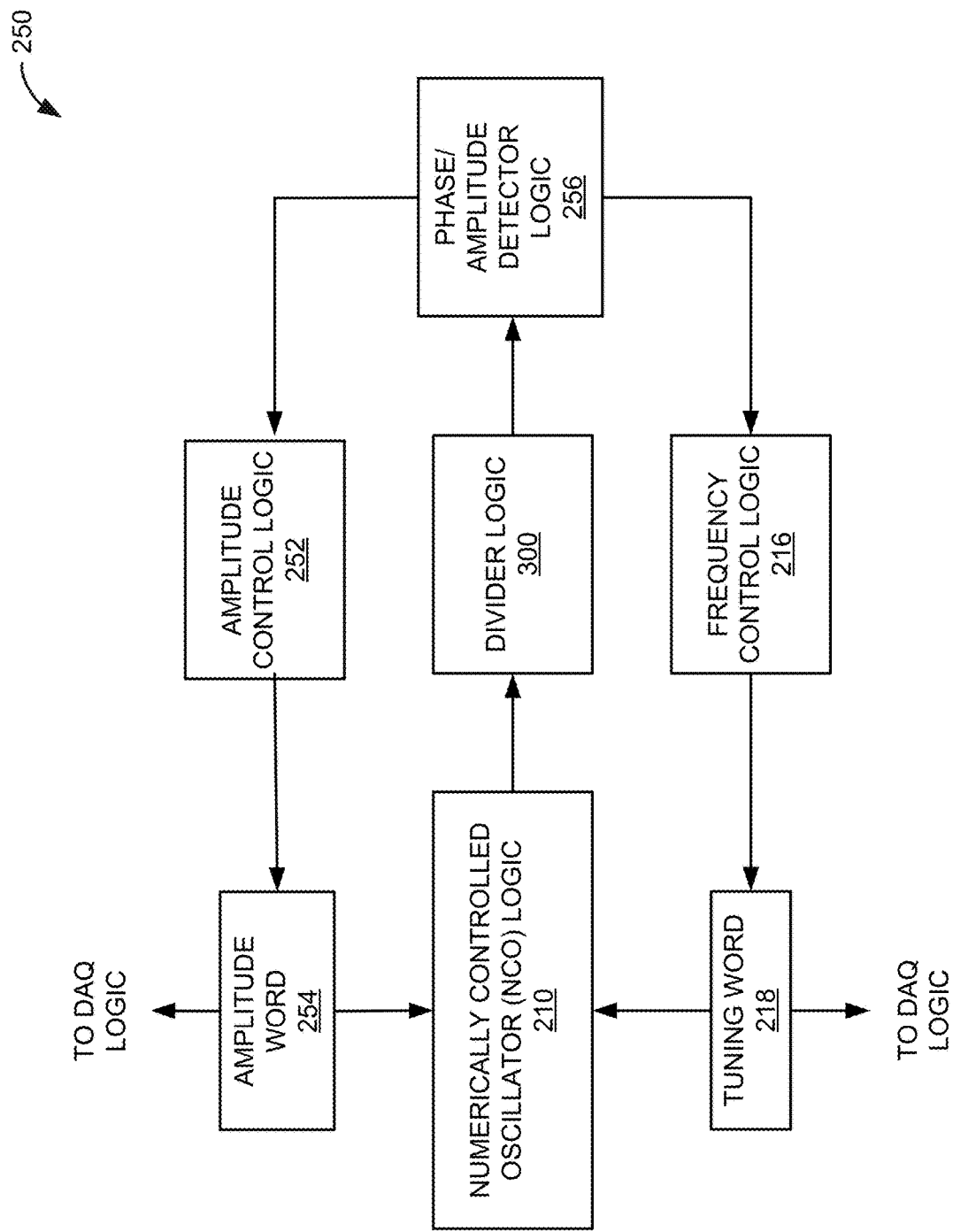

FIGS. 2A-B illustrate block diagrams of example embodiments of oscillator logic 120. Referring to FIG. 2A, an example embodiment 200 of oscillator logic 120 may include various components, such as numerically controlled oscillator (NCO) logic 210, divider logic 300, phase detector logic 214, frequency control logic 216, and tuning word 218.

The NCO logic 210 may include logic that may implement, for example, a digital signal generator. The NCO may include logic for generating a signal that may have a frequency and amplitude (e.g., a sinusoidal waveform). The frequency of the signal may be controlled by tuning word 218. The NCO logic 210 may include, for example, a phase accumulator (PA), a lookup table, and/or a digital to analog converter (DAC) that, in conjunction with the tuning word 218, are used to generate the signal. The NCO logic 210 may also include a filter (e.g., low-pass filter, bandpass filter) that may, for example, filter frequency-related harmonics that may otherwise be present in the generated signal.

The divider logic 300 may include provisions that may produce a measured signal and a reference signal. The measured signal may represent a signal generated by a sensor device. The reference signal may represent a reference used by detector logic that may be used to detect a difference in phase and/or amplitude between the measured signal and the reference signal. Details regarding divider logic 300 will be discussed further below with respect to FIG. 3.

The phase detector logic 214 may include provisions for identifying a difference in phase between the reference signal and the measured signal. These provisions may include logic for acquiring the measured signal and reference signal from the divider logic 300, comparing the measured signal with the reference signal, and identifying a difference between the phase of the measured signal and the phase of the reference signal based on a result of the comparison.

The frequency control logic 216 may include provisions for (1) acquiring the difference in phase between the measured signal and the reference signal identified by the phase detector logic 214 and (2) generating tuning word 218 based on the difference in phase.

Tuning word 218 may include information (e.g., data, control signals) that may, for example, be used to control the frequency of the signal generated by the NCO logic 210. The tuning word 218 may also include information that may be transferred to the DAQ logic 130 (FIG. 1). The DAQ logic 130 may process this information and provide it to the processing logic 140 which may use the information to identify a quality of material in a well containing the sensor device.

The following example may be helpful in understanding an operation of the above-described components. For example, referring to FIGS. 1 and 2A, suppose, for example, a sample containing living biological cells is added to a well containing the sensor device. Now suppose the sample interacts with (e.g., binds to) the sensor device and affects a resonant frequency and motional resistance of the sensor device based on a quality (e.g., coupled mass viscosity, density, viscoelasticity) of the biological cells.

NCO logic 210 may generate a signal at a predetermined frequency. The predetermined frequency may be generated based on a predetermined starting value of tuning word 218. The divider logic 300 may acquire the signal and apply it to the sensor device to generate a measured signal. In addition, divider logic 300 may generate a reference signal based on the signal acquired from the NCO logic 210. The phase detector logic 214 may detect a phase difference between the measured signal and the reference signal.

The frequency control logic 216 may generate a tuning word 218 based on the detected difference in phase. The generated tuning word 218 may reflect an update to a previous value of tuning word 218. The tuning word 218 may be transferred to the NCO logic 210 which may use the tuning word 218 to adjust, for example, the frequency of the signal generated by the NCO logic 210. Adjusting the frequency of the signal generated by the NCO logic 210 may accommodate finding a resonant frequency associated with the sensor device. In an embodiment, a resonant frequency of a sensor device is considered found when the detected difference in phase reaches zero.

In addition, the frequency control logic 216 may transfer the tuning word 218 to the DAQ logic 130. The DAQ logic 130 may acquire the tuning word 218 and transfer the tuning word 218 to the processing logic 140. The processing logic 140 may process the tuning word 218. This processing may include, for example, performing various calculations using the tuning word 218. These calculations may include, for example, identifying a resonant frequency associated with the sensor device. Moreover, the calculations may include identifying a quality of the biological cells contained in the well. Note that the DAQ logic 130 may process the tuning word 218. For example, in an embodiment, the DAQ logic 130 performs a fast integration of tuning words 218 and transfers the results to the processing logic 140. Integrating the tuning words 218 in this manner may obviate overwhelming the processing logic 140 with tuning words 218 acquired by the DAQ logic 130.

Referring now to FIG. 2B, another example embodiment 250 of oscillator logic 120 may include various components, such as NCO logic 210, divider logic 300, phase/amplitude logic 256, frequency control logic 216, tuning word 218, amplitude control logic 252, and amplitude word 254. The NCO logic 210, divider logic 300, frequency control logic 216, and tuning word 218 may include provisions similar to provisions described above for these components with respect to FIG. 2A.

The phase/amplitude logic 256 may include provisions for identifying a phase difference and an amplitude difference between the measured signal and reference signal that is provided by the divider logic 300. The identified phase difference may be transferred to the frequency control logic 216 which may generate and distribute tuning word 218, as described above.

The identified amplitude difference may be transferred from the phase/amplitude detector logic 256 to amplitude control logic 252. Amplitude control logic 252 may generate, for example, amplitude word 254 based on the identified amplitude difference. The amplitude word 254 may be transferred to the DAQ logic 130 which may provide the word to the processing logic 140. Here, the processing logic 140 may use the amplitude for identifying a motional resistance associated with the sensor device.

In addition, the amplitude word 254 may be transferred to NCO logic 210 which may use the amplitude word 254 to adjust amplitude of the signal generated by the NCO logic 210. Adjusting the amplitude of the signal may, for example, improve detection of reference signal and/or measured signal by the phase/amplitude detector logic 256.

Figure 3:
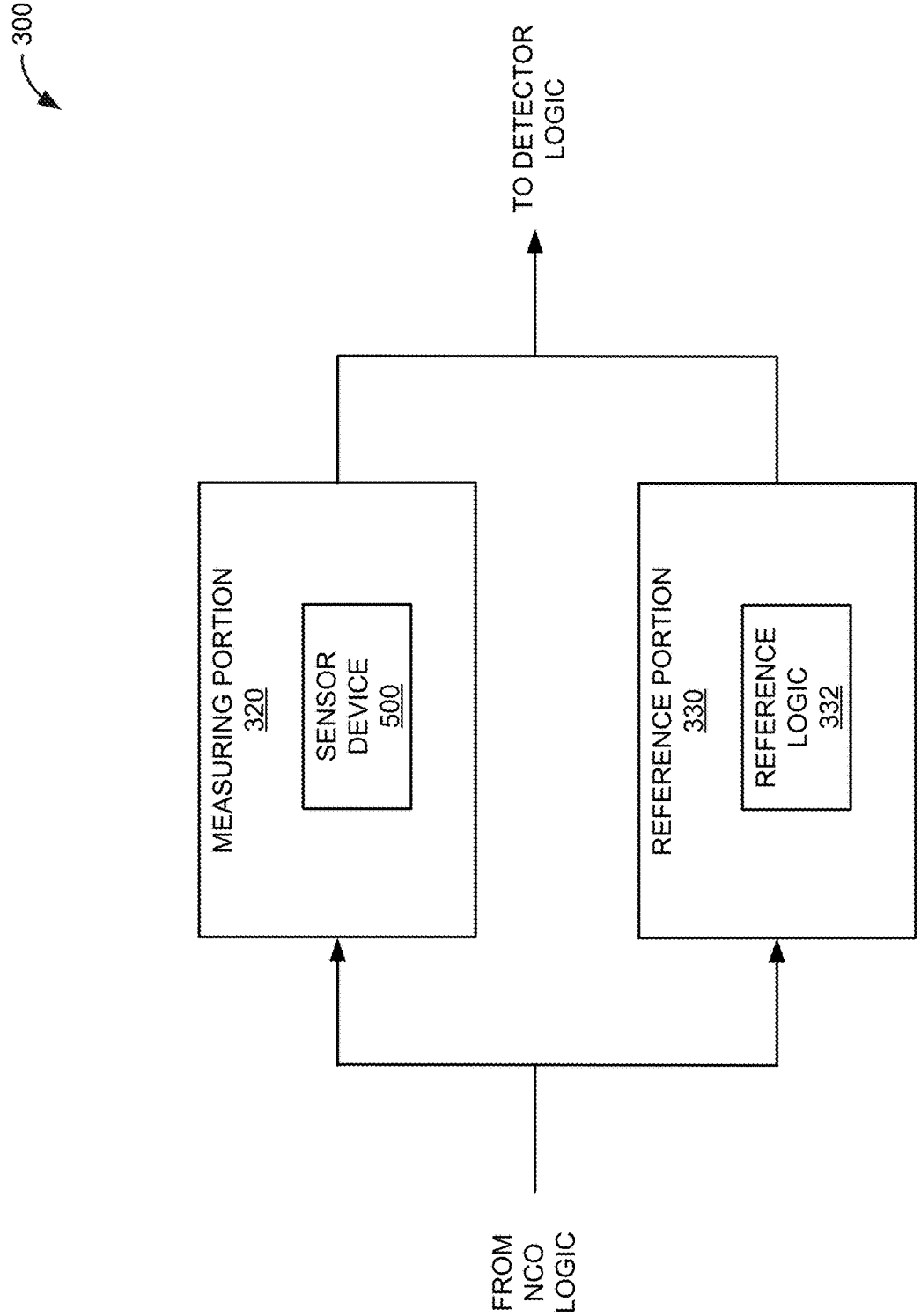
FIG. 3 illustrates an example block diagram of an embodiment of divider logic.

FIG. 3 illustrates a block diagram of an example embodiment of divider logic 300. Referring to FIG. 3, divider logic 300 may include various components, such as, for example, a measuring portion 320 and a reference portion 330.

The measuring portion 320 may include a sensor device 500. An example embodiment of sensor device 500 will be described further below with respect to FIG. 5. Measuring portion 320 may also include logic that may acquire the signal generated by the NCO logic 210, apply the signal to the sensor device 500, acquire a signal from the sensor device 500 that represents a measured signal, and transfer the measured signal to detector logic (e.g., phase detector logic 214, phase/amplitude detector logic 256) for further processing.

The reference portion 330 may include logic that may acquire the signal generated by the NCO logic 210, apply the signal to reference logic 332, and acquire a signal from the reference logic 332 that represents a reference signal. The measuring portion 320 may also include logic for transferring the reference signal to the detector logic (e.g., phase detector logic 214, phase/amplitude detector logic 256) for further processing, such as described above.

For example, suppose that sensor device 500 includes a QCM crystal. Measuring portion 320 may acquire a signal generated by NCO logic 210 and apply the acquired signal to the QCM crystal. The QCM crystal may produce a measured signal in response to the applied signal. The measuring portion 320 may transfer the measured signal to detector logic (e.g., phase detector logic 214, phase/amplitude detector logic 256), which may further process the measured signal.

Now suppose, for example, that reference logic 332 includes a capacitor that represents a parasitic capacitance associated with the sensor device 500. Reference portion 330 may acquire a signal generated by NCO logic 210 and apply the acquired signal to the capacitor. The capacitor may produce the reference signal in response to the applied signal. The reference portion 330 may transfer the reference signal to detector logic (e.g., phase detector logic 214, phase/amplitude detector logic 256), which may further process the reference signal.

Figure 4A:
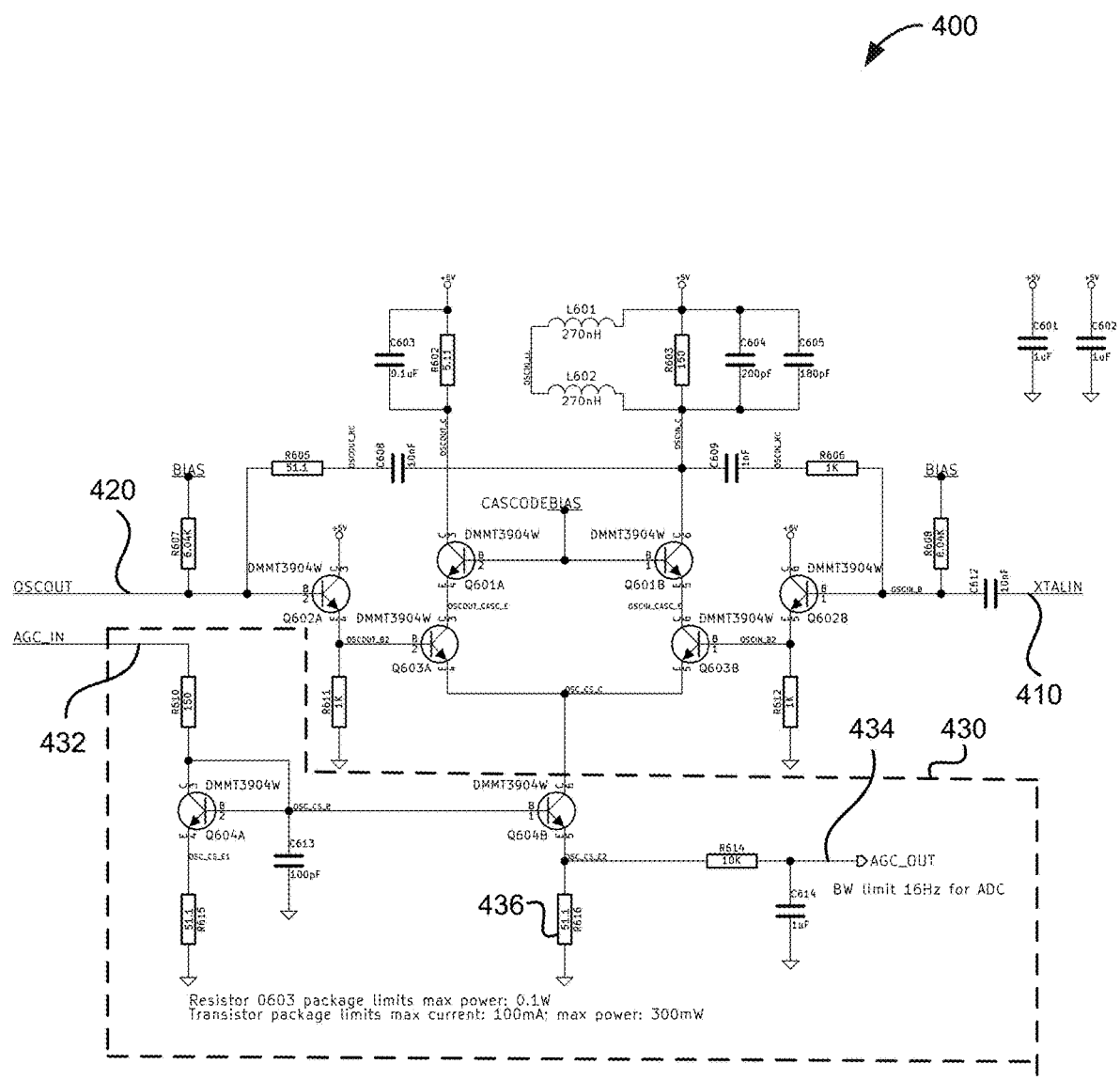
FIGS. 4A-B illustrate example logic that may be used to implement an oscillator that may be associated with a sensor device.
Figure 4B:
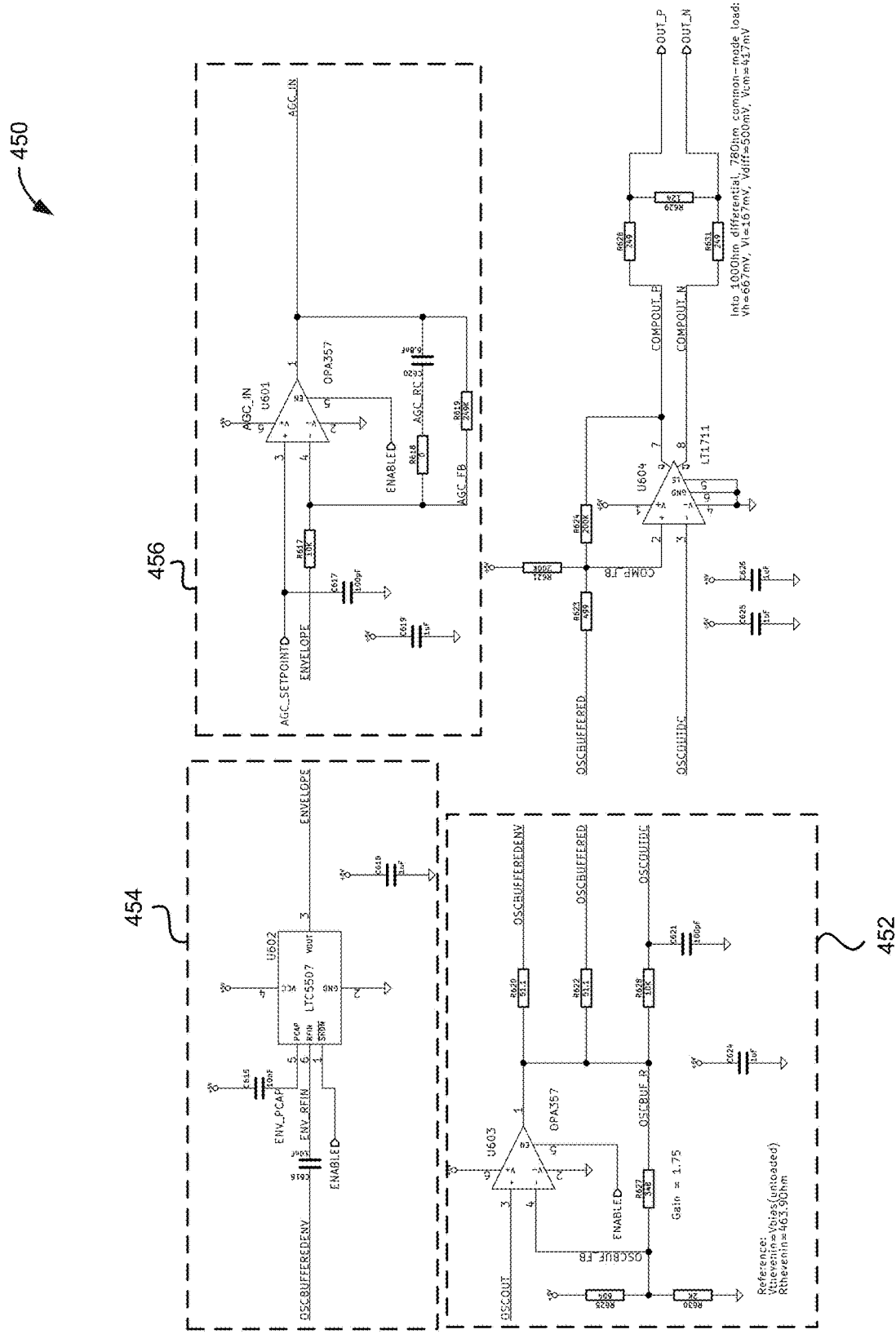

FIGS. 4A-B illustrates example logic 400, 450 that may be employed in an embodiment of system 100 that utilizes an oscillator to identify a resonant frequency and motional resistance associated with a sensor device. Referring to FIG. 4A, logic 400 may include input 410, output 420, and current source circuitry 430. The input 410 may produce a signal (e.g., voltage) to excite, for example, a QCM crystal that may be contained in the sensor device. In addition, input 410 may receive a signal produced by the QCM crystal in response to exciting the QCM crystal.

Logic 400 may generate a sine wave having a frequency that may be determined based on the signal received from the QCM crystal. The sine wave may be output as signal OSCOUT via output 420. A resonant frequency of the QCM crystal may be determined based on the sine wave. This resonant frequency may change based on, for example, a quality of living biological cells that may be contained in a well that includes the QCM crystal.

Current source circuitry 430 may include circuitry for biasing Q601A, Q601B, Q603A, and Q603B. The current source circuitry 430 may act to provide a current mirror. Current source circuitry 430 may include an AGC input 432 and an AGC output 434. An AGC_OUT signal may be produced at AGC output 434. The AGC_OUT signal may include a voltage that is based on a voltage ($V_{RE}$) associated with emitter resistor 436. Note that V may be proportional to a bias current for Q601A, Q601B, Q603A, and Q603B that may flow through Q604B's emitter resistor 436.

Referring now to FIGS. 4A and 4B, circuitry 450 may include a buffer 452, envelope detector 454, and error amplifier 456 in a control loop from OSCOUT to AGC_IN. The buffer 452 acts as a buffer for OSCOUT. Specifically, buffer 452 acquires OSCOUT and produces a signal (OSCBUFFEREDENV) based on the OSCOUT signal. OSCBUFFEREDENV is fed to the envelope detector 454 which produces a signal (ENVELOPE) that reflects an amplitude of OSCBUFFEREDENV. Error amplifier 456 compares ENVELOPE to a predetermined set point signal (AGC_SETPOINT) and produces signal AGC_IN based on the comparison. AGC_IN is fed into circuitry 400 (FIG. 4A) at input 432 in order to adjust the amplitude of OSCOUT and keep the amplitude constant.

Now referring to FIG. 4A as noted above, signal AGC_OUT may be output via the AGC output 434. The AGC_OUT signal may act as a measurement point. The AGC_OUT signal may be transferred to an analog-to-digital converter (ADC) that may be contained in DAQ logic 130. The AGC_OUT signal may be used to determine a bias current flowing through an oscillator associated with circuitry 400 and 450. AGC_OUT may be used to derive the $R_m$ ($\Delta R$) of a QCM associated with logic 400. For example, in an embodiment, as $R_m$ of a QCM increases, output amplitude of OSCOUT may decrease. In response, the AGC increases its output voltage, increasing bias current (e.g., at Q604B) until an amplitude at OSCOUT returns to the set value. The bias current is measured as voltage drop across emitter resistor 436. It may act, for example, as an indirect indicator of $R_m$ for a QCM crystal that may be associated with the oscillator. The AGC_OUT signal may be a voltage that is based on a voltage ($V_{RE}$) associated with emitter resistor 436. The AGC_OUT signal may be used by system 100 to measure $R_m$ associated with the QCM crystal.

For example, referring to FIGS. 1 and 4A-B, suppose that the AGC_OUT signal is a voltage based on $V_{RE}$. The voltage may be measured by DAQ logic 130 which may generate a value (e.g., binary number) that represents the measured voltage. The generated value may be transferred to the processing logic 140 which may identify $R_m$ associated with the QCM crystal based on the generated value. Note that $R_m$ may act as an electrical equivalent for the dampening based on a model (e.g., Butterworth-Van Dyke (BVD) model).

Figure 5:
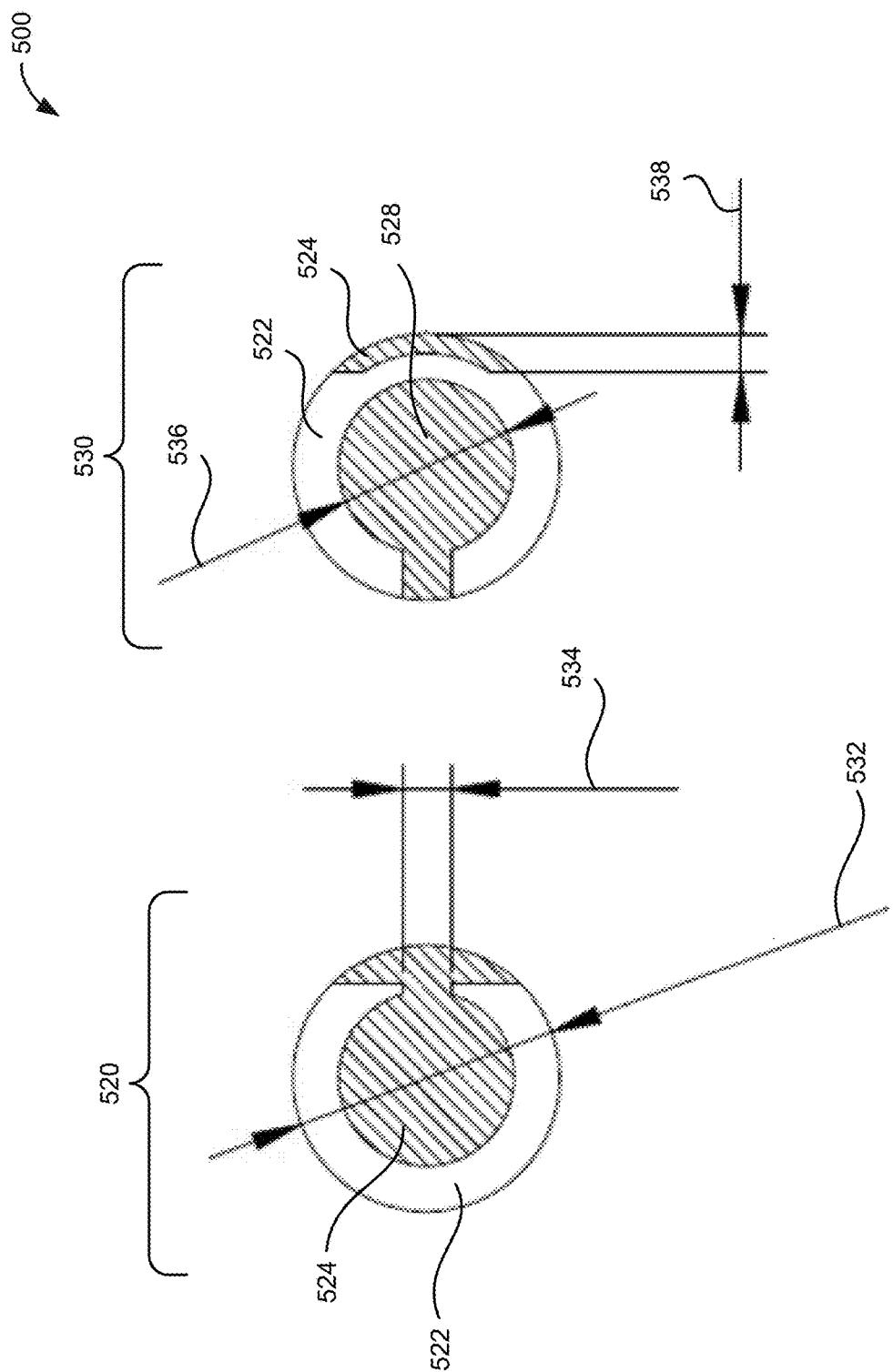
FIG. 5 illustrates an example embodiment of a sensor device.

FIG. 5 illustrates an example embodiment of a sensor device 500 that may be used with techniques described herein. The sensor device 500 may operate in accordance with various QCM principles. Referring to FIG. 5, a first view 520 and a second view 530 of sensor device is shown. The first view 520 may include a first electrode 524 and a crystal 522, and the second view 530 may include a second electrode 528. Note that the first electrode 524 may wrap around the crystal 522 from the first view 520 to the second view 530.

The crystal 522 may exhibit piezoelectric properties and the electrodes 524, 528 may be electrical conductors. In an embodiment, crystal 522 is a quartz crystal and electrodes 524, 528 are gold-plated electrical conductors.

Sensor device 500 may be associated with various dimensions 532, 534, 536, and 538. In an embodiment, these dimensions are 15.69 millimeters (mm), 2.5 mm, 9 mm, and 2 mm, respectively.

In combination, the crystal 522 and electrodes 524, 528 may enable sensor device 500 to operate in accordance with QCM principles. More specifically, material (e.g., living biological cells) may bind to a portion of the first electrode 524 shown in the first view 520. This binding of the material may affect a motional resistance and resonant frequency of the sensor device 500. The motional resistance and resonant frequency may be measured by external logic that may connect to the sensor device 500 at electrodes 524 and 528 shown in the second view 530.

A sensor device 500 may be included in a multi-well assembly. The multi-well assembly may be used to hold one or more experiments associated with identifying qualities of biological cells.

Figure 6:
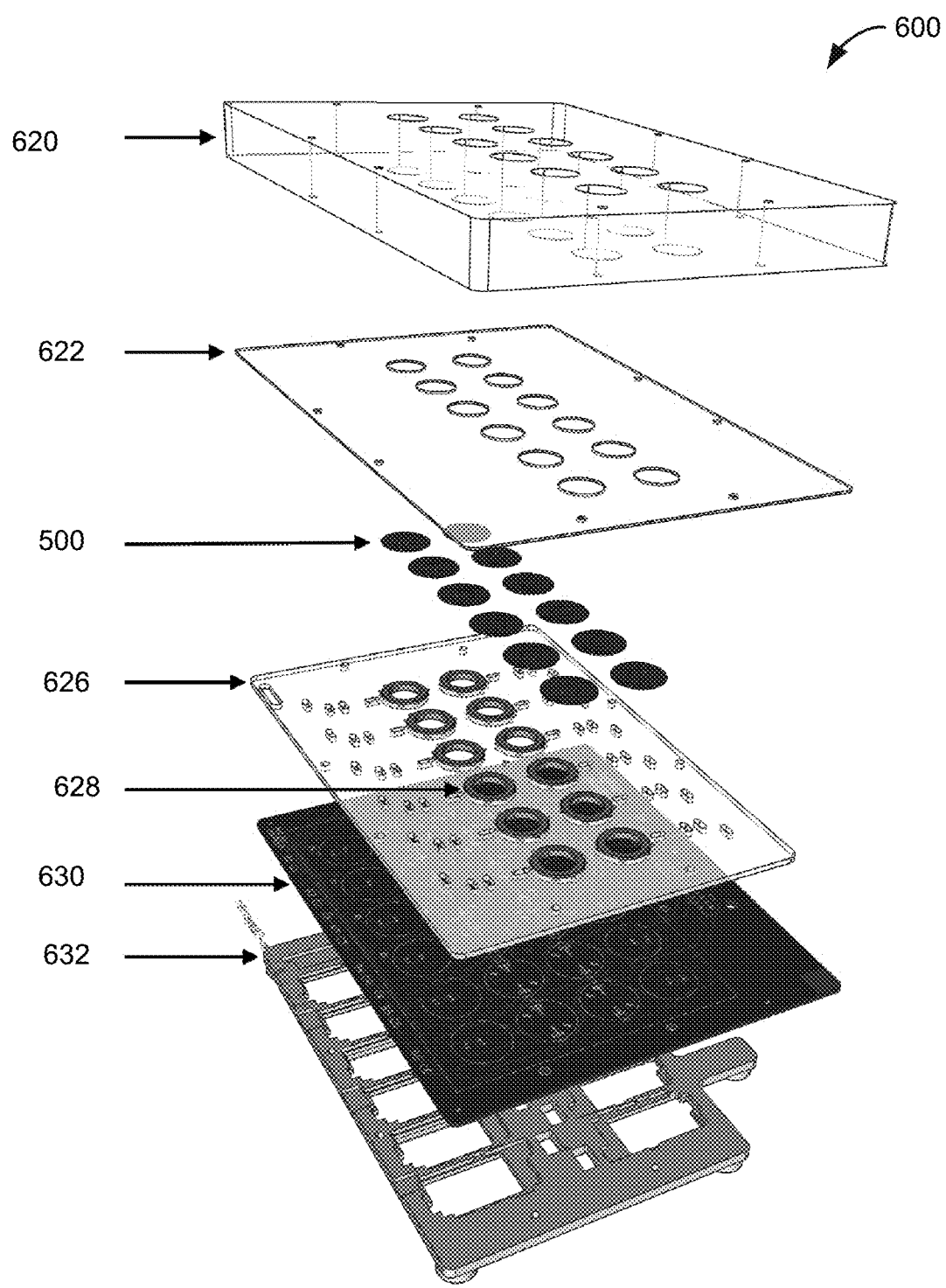
FIG. 6 illustrates an example of a multi-well assembly.

FIG. 6 illustrates an example of a multi-well assembly 600 that may be used with techniques described herein. Referring to FIG. 6, the multi-well assembly 600 may include a plurality of components such as, for example, a well plate 620, a seal 622, sensor devices 500, a mid-guide 626, sensor device connectors 628, a PCB 630, and a stiffener 632.

The QCM well plate 640 may include a number of wells for receiving the sensor devices 500. The QCM well plate 640 may be made from an acrylic material although other materials may be used. In an embodiment, the QCM well plate 640 includes provisions for accommodating 12 sensor devices 500.

The seal 622 may act as a seal (e.g., water proof seal) between the QCM well plate 640 and the sensor devices 500. In an embodiment, the seal 622 is a Federal Drug Agency (FDA) compliant silicone rubber transparent film. One side of the seal 622 may include an adhesive that enables the seal 622 to adhere to the well plate 620. Moreover, the seal 622 may include one or more holes that may align to one or more holes contained in the well plate 620.

The sensor devices 500 may include crystals that may respond to various qualities associated with living biological cells contained in the wells such as described above. A sensor device 500 may be positioned such that a center portion of its first electrode 524 (FIG. 5), as shown in the first view 520, may be present in a well contained in the well plate 620 and electrodes 524, 528, as shown in the second view 530 may make electrical contact with a sensor device connector 628.

The mid-guide 626 may act as a guide for the sensor device connectors 628. The mid-guide 626 may include a plurality of holes that may be used to shape and guide the sensor device connectors 628 to ensure the sensor device connectors 628 and sensor devices 500 are properly aligned to enable signals to be transferred between the sensor devices 500 and the PCB 630.

A sensor device connector 628 may include a flexible electrically conductive connector that may be electrically connected to a sensor device 500. The sensor device connector 628 may act to electrically connect the sensor device 500 with the PCB 630 and enable signals to be transferred between the sensor device 500 and the PCB 630. An example of a connector that may be used to implement sensor device connectors 628 is the Fujipoly Zebra™ connector available from Fujipoly America Corporation, Carteret, N.J.

In an embodiment, sensor device connectors 628 includes an elastomer and an electrically conductive component (e.g., silver) that enables the sensor device connector 628 to electrically conduct the signals from the PCB to the sensor device 500 after the sensor device connector 628 is compressed. Here, the sensor device connector 628 may be shaped to form a hollow cylinder. Compressing the hollow cylinder may cause the sensor device connector 628 to become electrically conductive. Electrical continuity between the sensor device 500 and the PCB 630 may be accommodated by positioning the electrodes 524 and 528 in the second view 530 to make electrical contact at one end of the cylindrically-shaped sensor device connector 628 and positioning the PCB 630 to make electrical contact at an opposite end of the cylindrically-shaped sensor device connector 628. The sensor device connector 628 may include alternating conducting and non-conducting layers that may cause the sensor device connector 628 to conduct the signals in one direction from the PCB 630 to the sensor device 500 after the sensor device connector 628 is compressed.

The PCB 630 may include electrically conductive connections that may connect to sensor devices 500 at electrodes 524, 528 in the second view 530. In addition, the PCB 630 may contain provisions that may provide an electrical path for transferring signals generated by the sensor devices 500 to be transferred to logic external to the multi-well assembly 600. For example, the PCB 630 may include provisions for transferring signals from the sensor devices 500 to divider logic 300 (see FIGS. 2A-B and 3). Embodiments of PCB 630 may also include oscillator logic and/or environmental sensors, such as described above.

In an embodiment, the PCB 630 may include a conformal coating that may act to protect circuits contained on the PCB 630 against malfunctions (e.g., damage due to corrosion, electrical shorts) that may be caused by, for example, salts and/or moisture. Electrical contact areas connector for sensor device connectors 628 and PCB connectors to the outside world are masked and not coated. Examples of conformal coating that may be used include Parylene™, silicone, and/or urethane, although other suitable conformal coatings may be used.

The stiffener 632 may act as a support for the PCB 630 as well as the multi-well assembly 600. One side of the stiffener 632 may include feet (e.g., rubber feet) that may be used to stabilize the multi-well assembly 600. Note that stiffener 632 may include other mechanisms for stabilizing the multi-well assembly 600.

The multi-well assembly 600 may be assembled as follows. The seal 622 may be combined with the well plate 620 such that holes in the seal 622 are aligned with holes in the well plate 620. The seal 622 may include an adhesive that may enable the seal 622 to adhere to the well plate 620 and maintain alignment of holes in the seal 622 with the holes in the well plate 620.

The mid-guide 626 may then be placed and aligned on the seal 622. The sensor devices 500 and sensor device connectors 628 may be placed and aligned in the mid-guide's 626 holes. The PCB 630 may then be aligned such that one end of the sensor device connectors 628 makes appropriate electrical contact with electrical connectors on the PCB 630. Afterwards, the stiffener 632 may be aligned and placed on the PCB 630. Fasteners (e.g., screws, nuts and bolts, snaps) may be used to hold the assembly 600 together.

The multi-well assembly 600 may be built to function in a cell culture incubator. The incubator may provide an environment that may be native to a sample of, for example, living biological cells contained the multi-well assembly 600. For example, in an embodiment, multi-well assembly is built to function in an environment where temperatures may be at 37 degrees Celsius (C) or below, the air may be at 10 percent carbon-dioxide ($CO_2$) or below, and a relative humidity may be at 95 percent or below. Providing an environment that is native to the sample, may allow the sample to perform inherent physiological functions. The well format of the multi-well assembly 600 may allow for ample cell culture media to be maintained in the well, for ideal continued growth or maintenance conditions for the sample.

System 100 may provide a web graphical user interface (GUI). The web GUI may provide control of data acquisition hardware and real-time visualization of the acquired data. In an embodiment, the web GUI is based on hypertext markup language version 5 (HTML5) and JavaScript running on a client (web browser) that is executed by computer system 160. Processing logic 140 may execute a PHP-enhanced HTTP (hypertext transfer protocol) server. The visualized data may include a frequency and resistance/dampening against time and against each other.

The web GUI may include code (e.g., JavaScript code) that may be executed by computer system 160. The code may acquire (e.g., read, receive) data from the database server executed by the processing logic 140. The code may, for example, display graphics (e.g., circles, lines, text) to represent the acquired data on an output device (e.g., screen) contained in computer system 160. The graphics may be scalable vector graphics that may display and/or scale at various resolution/zoom combinations.

Data stored in the database may be provided by processing logic 140 to various tools that are executed by computer system 160. For example, as noted above, the database contained in processing logic 140 may be a MySQL database. Processing logic 140 may execute a MySQL server to store the acquired data and serve the data to computer system 160.

Computer system 160 may execute data analysis tools that may interface with the MySQL server and access the data via the MySQL server. Examples of tools that may be used include Microsoft Excel® and OriginPro®. Microsoft Excel® is available from Microsoft Corporation, Redmond, Wash. OriginPro® is available from OriginLab Corporation, Northampton, Mass. These tools may be used with middleware that may include provisions for interfacing with the MySQL server. For example, these tools may be used with Microsoft's Open Database Connectivity (ODBC) middleware as the conduit for the data. It is also possible to use other applications. Other applications may access the MySQL database directly using their "native" drivers or use ODBC as their conduit.

Figure 7:
FIG. 7 illustrates an example display of information that may be provided by a web interface.

FIG. 7 illustrates an example display 700 of information that may be provided by a web interface that may be contained in system 100. Referring to FIG. 7, example data acquired by DAQ logic 130 from the oscillator logic 120 and stored in the database contained in processing logic 140 is shown in three projections are provided. These projections show the acquired data in three dimensions.

Figure 8:
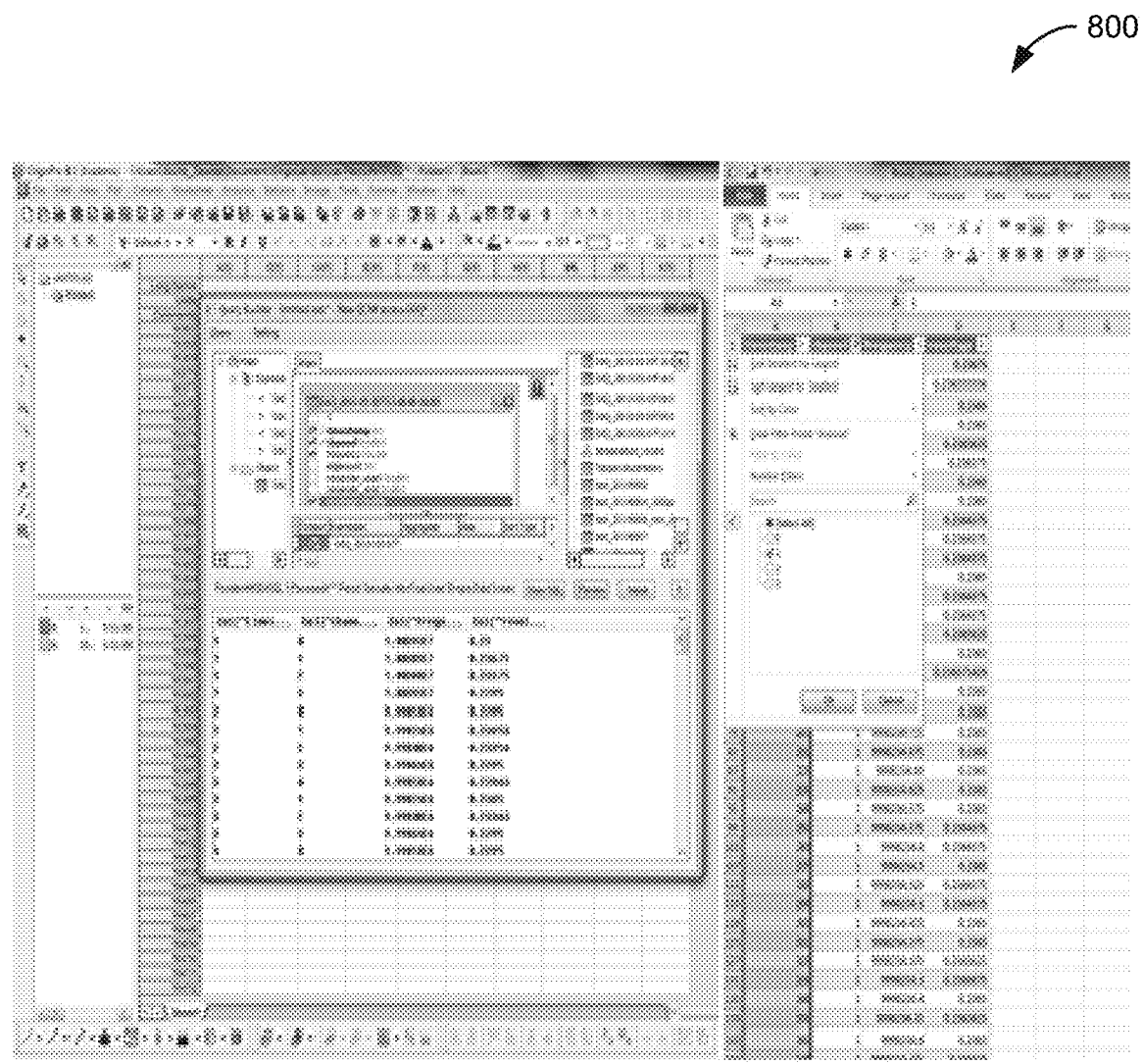
FIG. 8 illustrates example displays that may be provided by various tools described herein.

FIG. 8 illustrates example displays 800 that may be provided by the above-described tools. Specifically, FIG. 8 illustrates screenshots of Microsoft Excel® and OriginPro® accessing a database that may be contained in, for example, processing logic 140.

Now, referring back to FIGS. 1, 4A, and 5, a motional resistance ($R_m$) of a sensor device, such as sensor device 500 (FIG. 5), may be calculated from a signal output from AGC output 434 (FIG. 4A). A linear relationship between this signal and $R_m$ may be expressed, for example, by the equation $R_m = m * AGC\_OUT + b$. The relationship may be determined by using a dry clean sensor device 500, and observing $V_{RE}$ while performing a sucrose test (described further below). Data from the observation may be fitted to published values using density, viscosity, and the Muramatsu equation (also described further below). In an embodiment, the values of "m" and "b" were determined to be around 14000 Ohms/Volt and around −2900 Ohms, respectively.

The sucrose test may be used to identify "m" and "b" values for each well contained in a multi-well assembly 600. Identifying the "m" and "b" values for a well may be considered calibrating the well. The identified "m" and "b" values and the value of V may be used to calculate $R_m$. An example formula for conversion of $V_p$ to $R_m$ signal given "m" and "b" values of 14005.39893942 and −2919.681692418, respectively, to $R_m$ may be:

$$R_m = 14005.39893942 * V_{RE} - 2919.681692418$$

Referring now to FIGS. 1 and 6, samples to be measured may be placed in a multi-well assembly 600. The oscillator logic 120 (containing the multi-well assembly 600) may be located in an incubator and connected to the DAQ logic 130 through, for example, twisted pair and ribbon cables although other suitable types and/or combinations of connections may be used. The DAQ logic 130 may be located externally from the incubator. Positioning the oscillator logic 120 (containing the multi-well assembly 600) in an incubator may allow for living biological cells to exist in a controlled environment that may mimic their natural state, thus allowing intracellular processes to occur in a natural manner. The processing logic 140 may be connected (e.g., via a data network) to the computer system 160.

The dry frequency of the QCM devices 500 and AGC_OUT may be measured. This measurement may be performed after power is applied to the oscillator logic 120, DAQ logic 130, and processing logic 140. In an embodiment, a sensor device 500 has a dry frequency of 10 MHz and AGC_OUT of 0.21V.

Figure 9A:
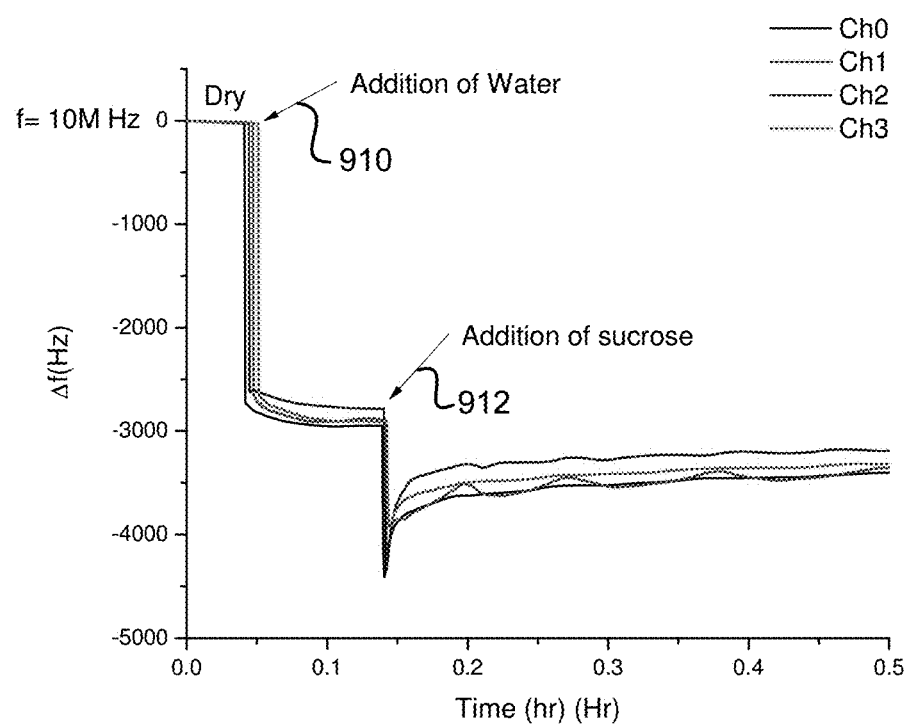
FIGS. 9A-I illustrate example graphs that may be generated by the DAQ system illustrated in FIG. 1.

Referring now to FIGS. 5 and 9A-I, aqueous sucrose solution may be considered a Newtonian fluid that produces a pure density-viscosity alteration with the $\Delta f$ and the $\Delta R$. $\Delta R$ may be measured indirectly. $V_{RE}$ may indicate the oscillator gain necessary to overcome a motional resistance of a given sensor device 500. The motional resistance may be directly related to $V_{RE}$, and may be calculated using a conversion formula individual to each well. FIG. 9A illustrates a graph that shows $\Delta f$ over time when water is added and afterwards a concentrated sucrose solution is added to achieve a 13% sucrose solution in a well.

In a first sucrose test it was verified that a dry sensor device 500 oscillated at the sensor device's 500 frequency (e.g., 10 MHz). At arrow 910, addition of double deionized water to a dry crystal resulted in the frequency shifting (e.g., 3000 Hz) for all the sensor devices 500. There may be a slight variation between the sensor devices 500 but that will be adjusted for when the sensor devices 500 are calibrated to each other using the sucrose test below. With the addition of a 13% w/v sucrose solution to the sensor devices 500 subsequent frequency changes were observed, as indicated at arrow 912.

Figure 9B:
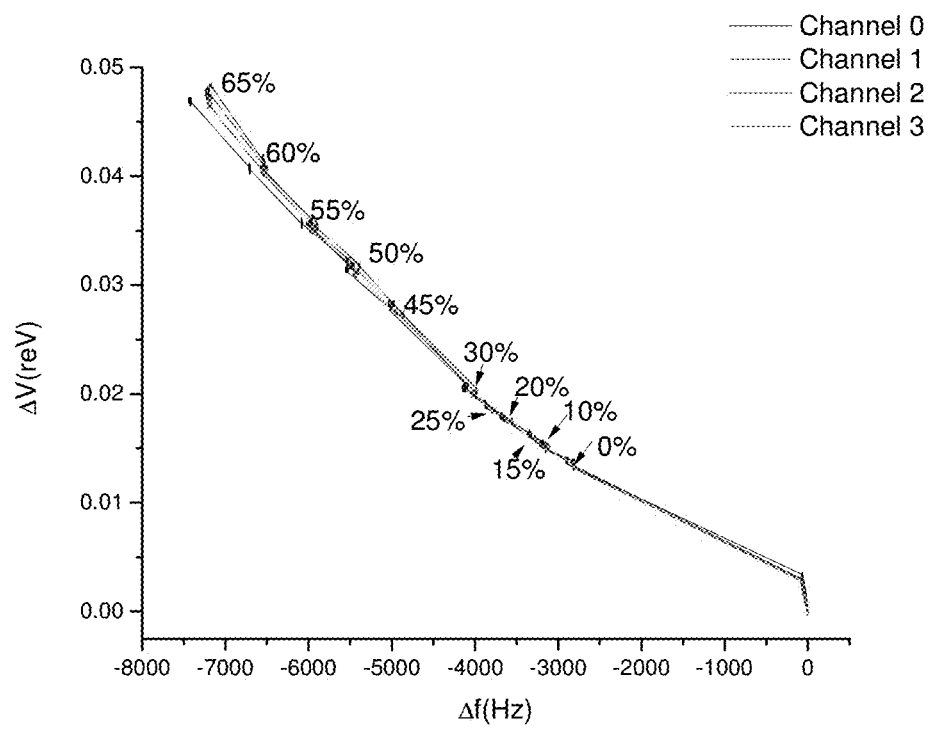

To calibrate the sensor devices 500 a systematic sucrose test may be carried out where different concentrations of sucrose solution are added to the wells containing the sensor devices 500 and the frequency and voltage measurements are recorded. FIG. 9B illustrates an example plot of $\Delta f$ and $\Delta V_{RE}$ starting with dry sensor devices 500 and then adding a 0-65% a sucrose solution to the wells containing the sensor devices 500. Note that pure density-viscosity dependencies of Δƒ and ΔR are exhibited which obey specific equations below.

The Kanazawa equation determined that the Δƒ is a function of the density of the liquid ($\rho_L$), the viscosity of the liquid ($\eta$), the frequency of oscillation of unloaded crystal ($f$), the density of quartz ($\rho q$), and shear modulus of quartz ($\mu q$)[1,8-10] and is as follows:

$$\Delta f = -f^{2/3}\left(\frac{\rho_L \eta}{\pi \mu \rho_q}\right)^{1/2}$$

Muramatsu then during his research in 1986 derived the equation that would determine the resistance in a liquid based system. ΔR may be a function of the frequency of oscillation of unloaded crystal ($f$), the viscosity of the liquid ($\eta$), the density of the liquid ($\rho_L$), electrode area (A), and electromechanical coupling factor (k) and is as follows:

$$\Delta R = (2\pi f \rho_L \eta)^{1/2} A/k^2$$

With these equations and the sucrose calibration curve, crystals may be calibrated so that they generate the same frequency and resistance readings as the equations predict. Also the conversion of the $\Delta V_{RE}$ may be calculated by manipulating the ΔR equation above.

After providing cells a varied surface during the plating process, the cells may bind equally to the crystals 522 or electrodes 524, or they can exhibit a binding preference. This binding preference may be important to know, since cells that are bound to the electrodes 524 may contribute to the signals produce by the sensor devices 500. The binding preference of the Bovine aortic endothelial cells (BAEC) was determined by replicating the cell attachment process and then staining the crystal with Coomassie Brilliant Blue which binds proteins in the cells revealing their binding location under a microscope. This technique may be used to determine that the cells bind to the electrodes 524 preferentially, meaning all the recorded signal can be attributed to the numbers of cells attached.

A test was performed where approximately 94,000 macrophage cells (DH82) were added to wells in system 100 a minimum of two hours after the sensor devices 500 had been treated with cell culture media. After a predetermined period of time (e.g., 24 hours) the cells were removed using trypsin and counted to determine the number of cells contributing to the signal, which was 120,000 DH82. The resulting changes in frequency are demonstrated in FIG. 9C which shows Δƒ over time. At the time of this test, the wells had not been calibrated. The displayed raw measurements show the small differences in circuit component and crystal manufacturing tolerances. These results will be calibrated after-the-fact.

Each well in system 100 may have associated logic 400 which in conjunction with a sensor device 500 (associated with the well) form an oscillator. System 100 may record $V_{RE}$ associated with the oscillators. A recorded $V_{RE}$, may be converted to resistance ($R_m$) using the formula below:

$$R_m = m * V_{RE} - b$$

Where "m" and "b" are per well calibration constants such as, for example, described above.

Figure 9C:
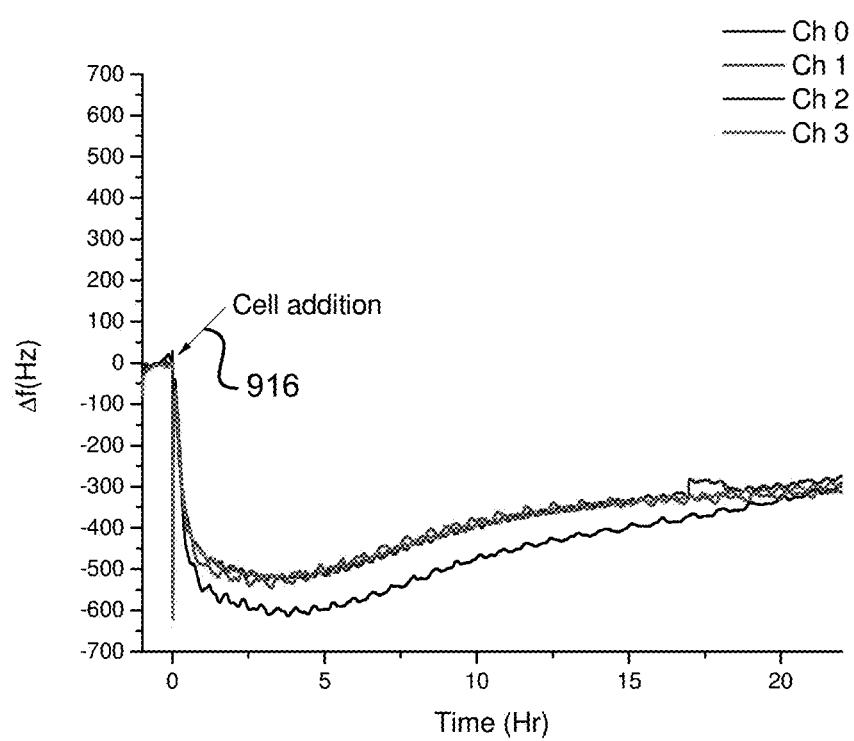
Figure 9D:
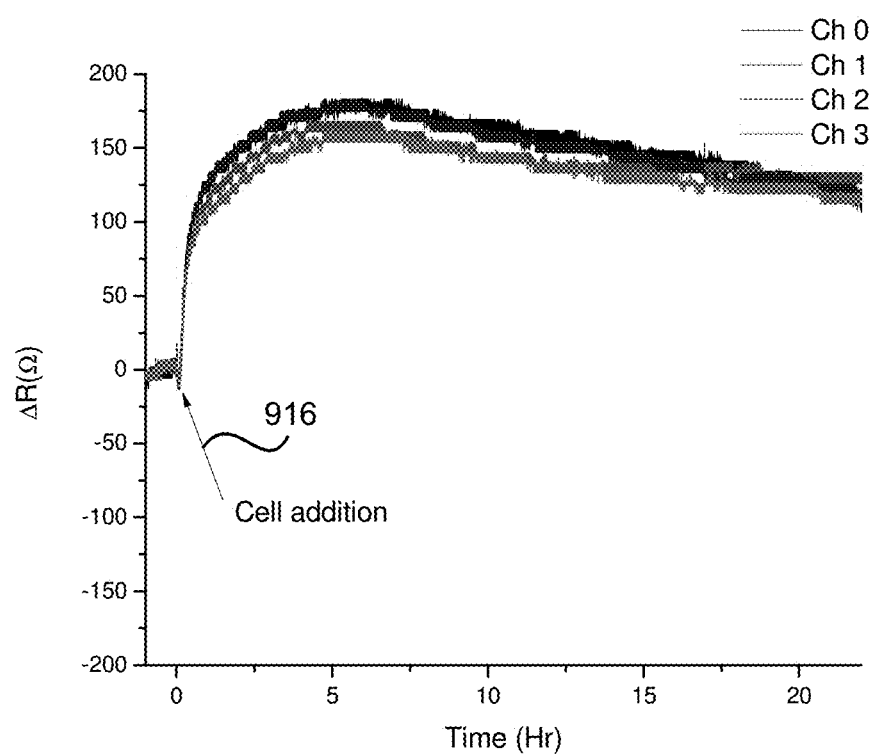

The motional resistance (also known as "dissipation") may quantify a dampening of the sensor device 500 and bound materials (e.g., bound cells), and provide viscoelastic information of the bound materials. Resistance may be measured in ohms (Ω) and is an inverse of the admittance of the sensor device 500. After the conversion is implemented using the acquired data the change in resistance (ΔR) may be graphed. FIGS. 9C and 9D illustrate example graphs of Δƒ and ΔR of a sensor device 500 in system 100 over time. Arrow 916 points to a time where cells (e.g., Bovine aortic endothelial cells) are added to wells in the multi-well assembly 600 and represent a standard adherent cell deposition and adherence pattern over the next 24 hours before coming to a steady state.

Figure 9E:
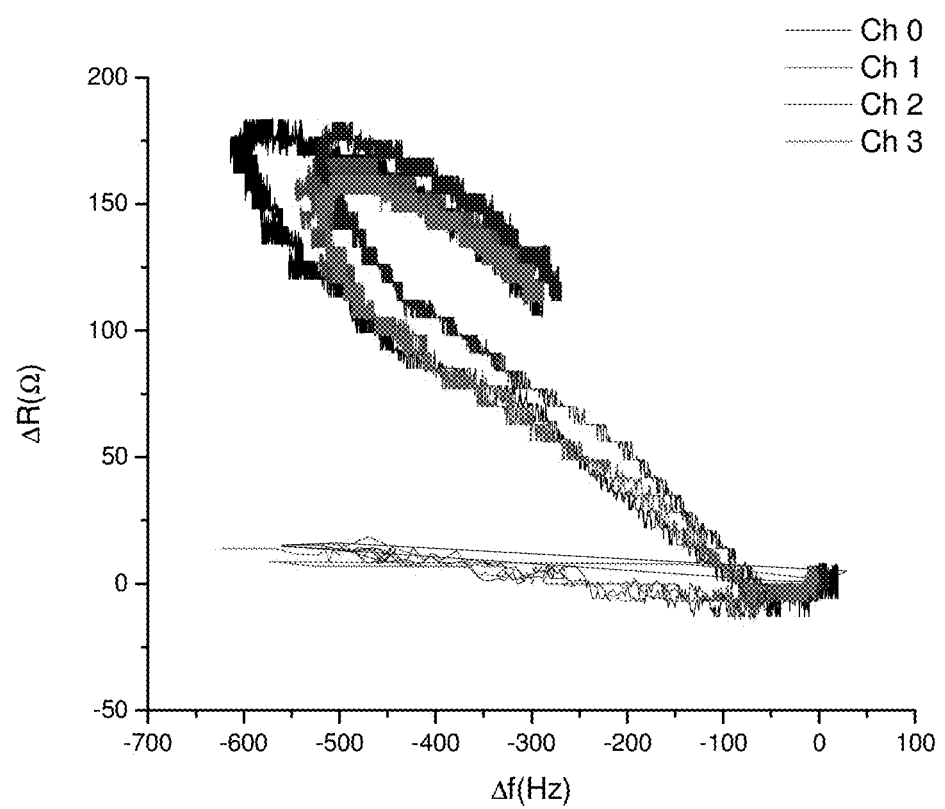

FIG. 9E illustrates a plot of the change in resistance and change in frequency data. This plot may reveal information regarding kinetic and mechanistic occurrences within the cell. Resistance (R) measurement of the sensor device 500 may be sensitive to cell density and cell-cell co-operation.

Figure 9F:
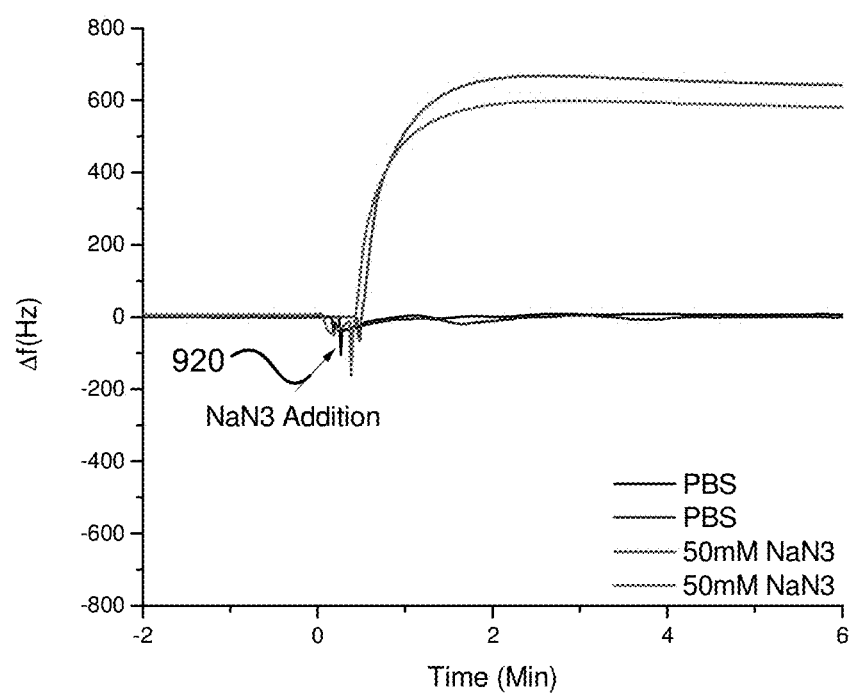

After cell deposition is complete (e.g., after 20 hours) and the cells have reached a stable equilibrium for some period of time (e.g., stable for 2 hours) then a treatment can be added to a well. FIG. 9F illustrates a time before treatment addition (e.g., -2 to -0 minutes), the treatment addition marked by the arrow 920, and the subsequent action of the treatment on the bound cells. In the case of FIG. 9F, 50 mM NaN₃ (Sodium Azide) or saline solution (PBS) (control) was added to two wells, respectively. Note that with the 50 mM NaN₃ addition there is a rapid rise in frequency that correlates to, for example, mitochondrial membrane depolarization. This rapid rise in frequency may predict chemically induced toxicity of macrophages, and their eventual death some time later (e.g., 24 hours later).

Figure 9G:
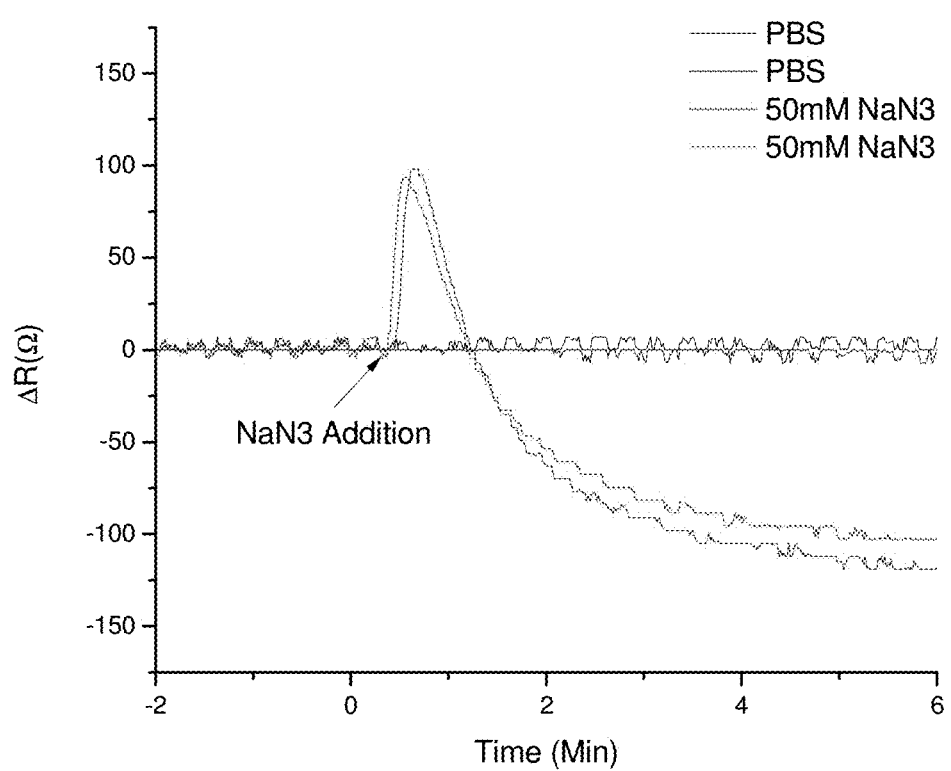

Oscillator logic 120 (FIG. 1) may capture motional resistance and provide a rich amount of information regarding mechanistic information like cell density and cell-cell cooperation. FIG. 9G illustrates that like the change in frequency in FIG. 9F, a treatment effect may be immediate, however within a period of time (e.g., 1.5 minutes) the resistance value may fall below a threshold value (e.g., zero). This is a very rapid R transient effect that may reverse rapidly, which could possibly correlate to an intracellular Ca2+ pulse that reverses quickly. Note that for Δƒ and ΔR the graphs illustrate time points that are of interest that may not be traditionally looked at in cell culture methods. In the case of sodium azide, the spike that is visible with the Δƒ and ΔR may not be detectable by other methods, and other methods may not be able to (e.g., not sensitive enough to) measure, for example, the response kinetics. Depolarization of the mitochondrial membranes may be visualized using mitochondrial dyes, however, these dyes typically are not quantitative.

Figure 9H:
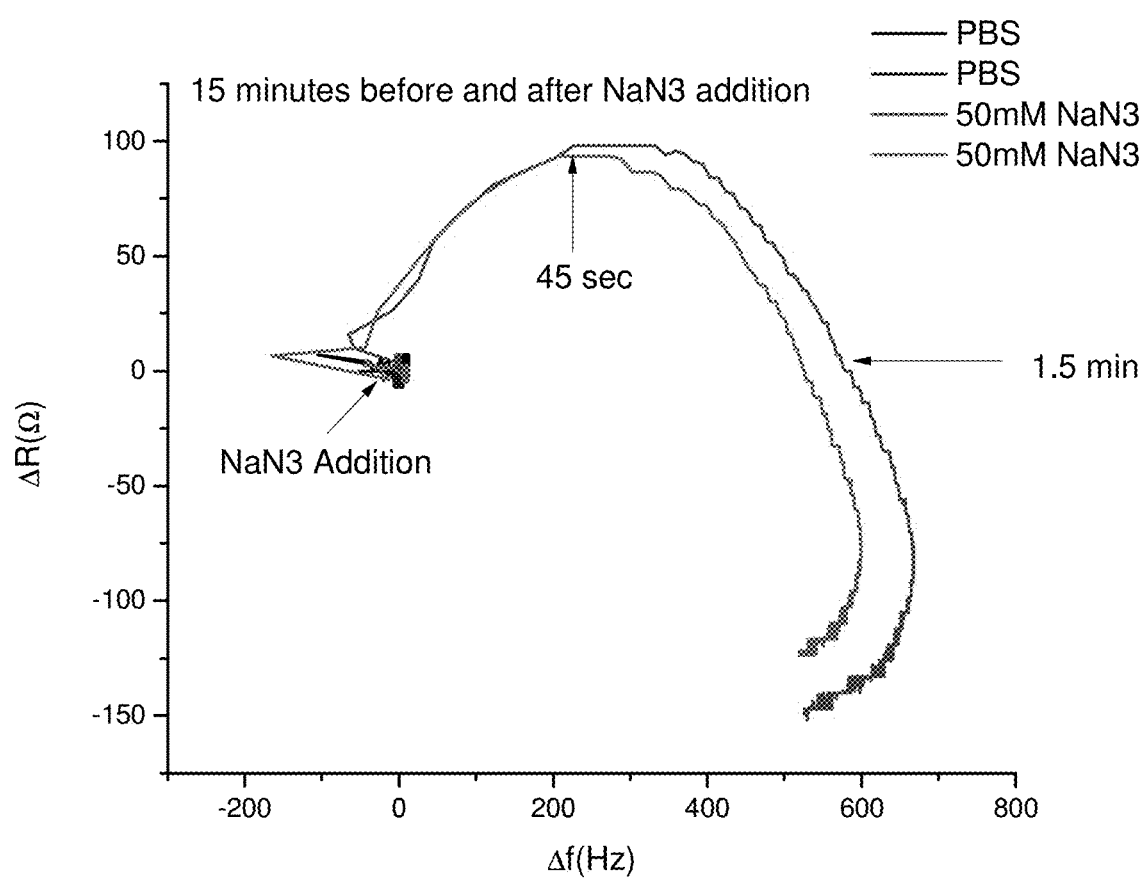

When the Δƒ vs. ΔR is plotted as illustrated in FIG. 9H, this creates a curve that displays changes in Δƒ vs. ΔR that result from sodium azide addition, which are distinct from the largely unchanged Δƒ vs. ΔR values for the saline solution (control). Note that the post treatment plot illustrated in FIG. 9H is distinct from that of cell adhesion shown in the graph in FIG. 9E.

Figure 9I:
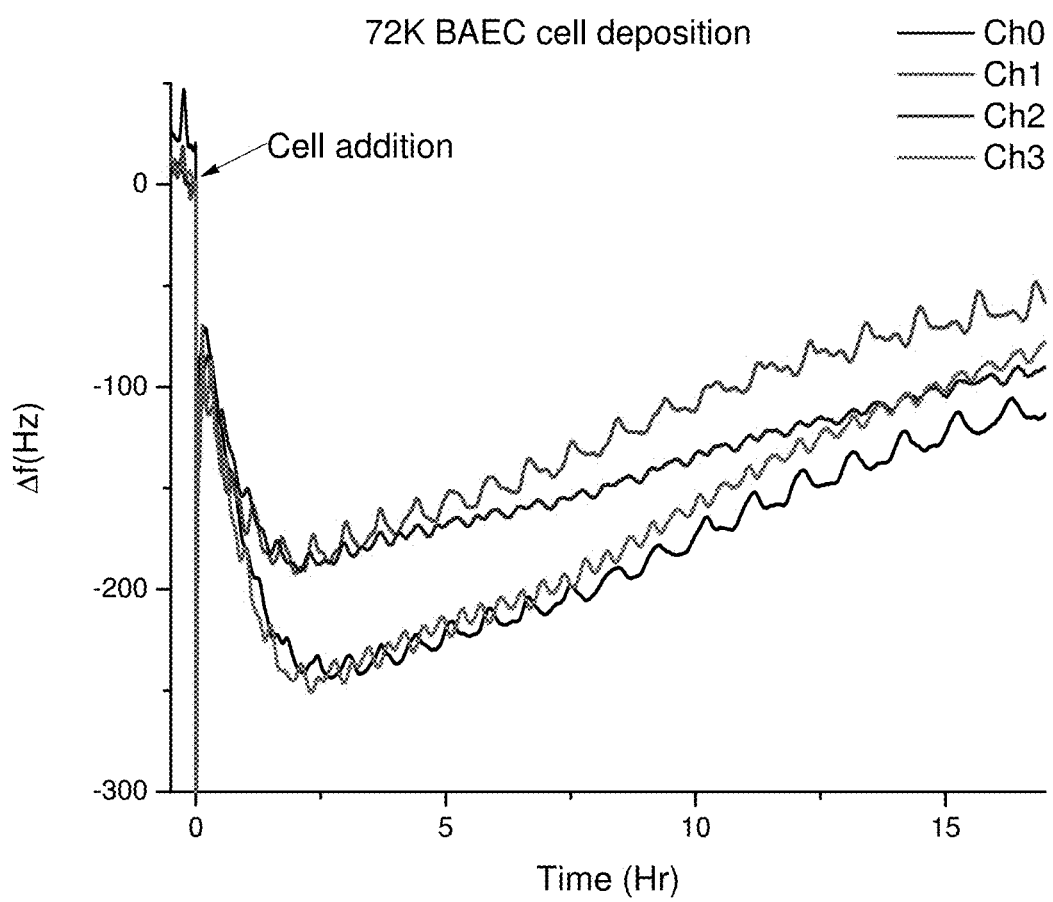

Seventy-two thousand Bovine Aortic endothelial cells were added to the wells in oscillator logic 120 a period of time (e.g., two hours) after wells containing the sensor devices 500 had been treated with cell culture media. The resulting changes in frequency is illustrated in FIG. 9I, demonstrating that the oscillator logic 120 may provide unique and distinct information regarding different cell types that correlate to their function and Biomolecular interactions. Sometime later (e.g., 24 hours later) the cells were removed using trypsin and counted to determine the number of cells contributing to the signal, which was 60,000 BAEC.

The multi-well assembly 600 can be used for pharmaceutical research to elucidate mechanism of action of a drug or toxicity. The multi-well assembly 600 when used in system 100 (FIG. 1) may provide an ability to run multiple wells that function in tandem at the same time, and that are calibrated to a standard, while acquiring real time data.

Figure 10:
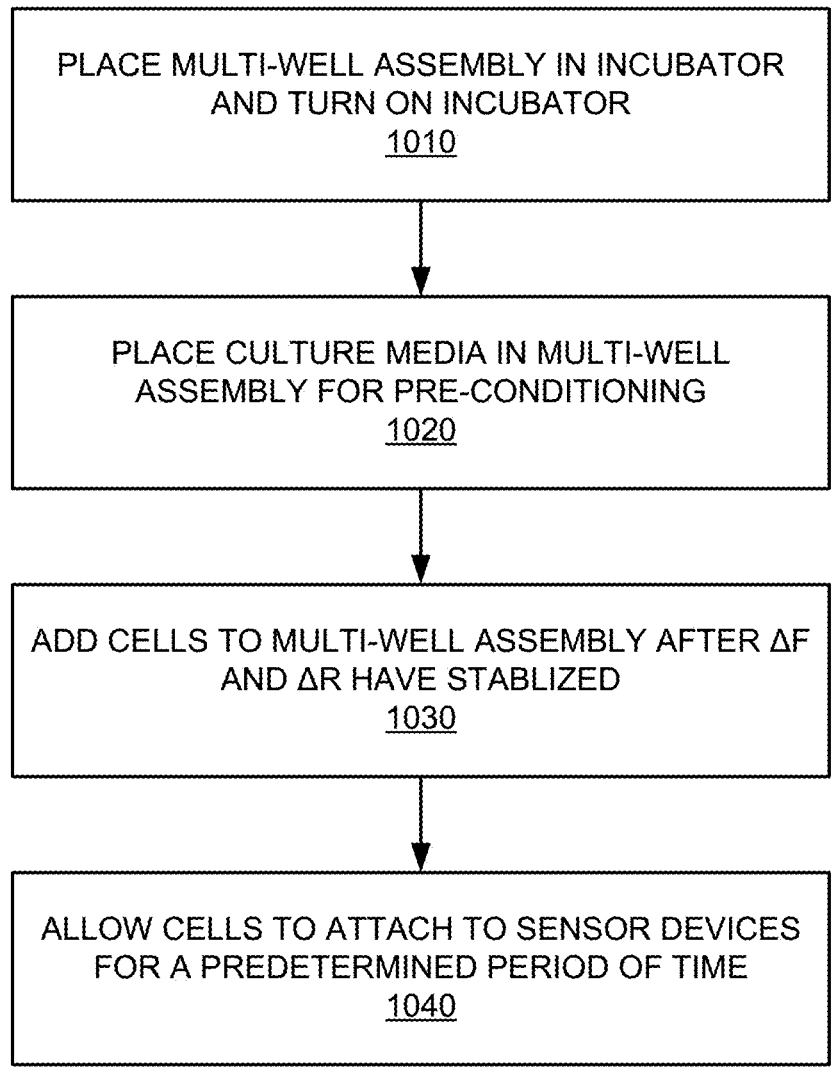
FIG. 10 illustrates a block diagram of an example experiment that may be performed using the DAQ system illustrated in FIG. 1.
Figure 11:
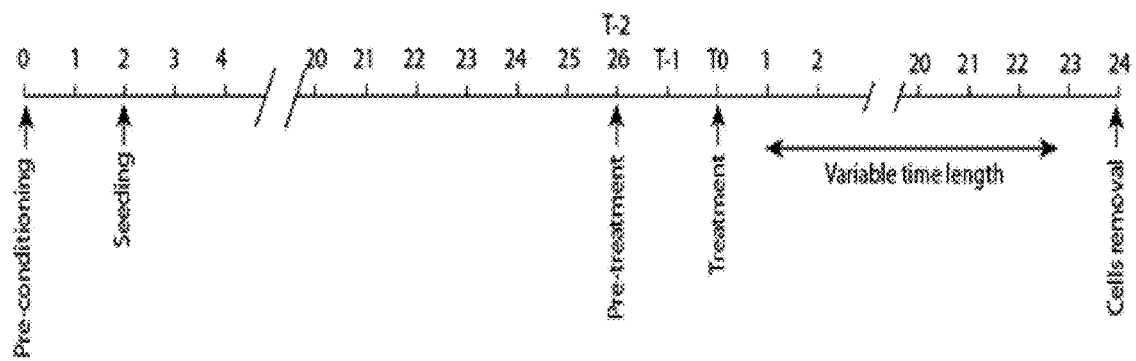
FIG. 11 illustrates an example time-line of the example experiment.
Figure 12:
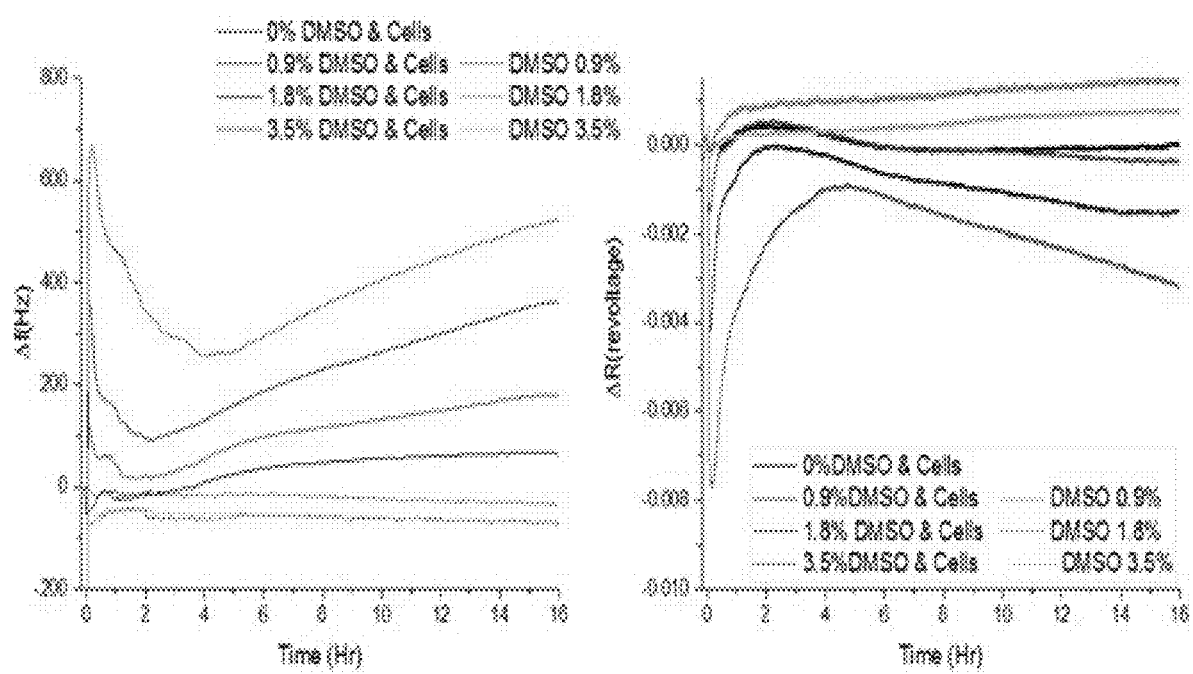
FIG. 12 illustrates example results from the experiment.

FIG. 10 illustrates a block diagram of an example experiment that may be performed using system 100. Referring to FIG. 10, an example experiment that may be performed using system 100 may involve, for example, placing the multi-well assembly 600 in the incubator and turning on the incubator (block 1010). Culture media is placed in the all the wells of the multi-well assembly 600 for pre-conditioning (block 1020). After the $\Delta f$ and $\Delta R$ traces have stabilized living biological cells are added (block 1030). The cells are allowed to attach to the sensor devices 500 for a predetermined period of time (e.g., between 24 to 72 hours, inclusive) (block 1040). The media is changed in preparation for the study. FIG. 11 illustrates an example time-line of the example experiment. FIG. 12 illustrates an example of results that may be produced from the experiment.

A unique ability of the multi-well assembly 600 is the ability to test multiple different dosages of a drug on a system that has all wells calibrated to each other. This removes the variability seen in other commercially available units that are run in tandem. Having multiple wells allows for untreated controls, and different dosages to be tested in duplicate or triplicate if needed. Yielding statistically significant data from just one experiment, which was previously not possible.

In the example experiment described above, toxicity due to drug suspension in Dimethyl Sulfoxide (DMSO) was suspected. The timing and the dosages that produced toxicity were not known. Testing of DMSO toxicity is not possible with optical systems due to its confounding ability to alter the refractive index. The multi-well assembly 600 overcomes this deficiency with optical systems and allows a way to measure the response of the cells to the drug.

The foregoing description of embodiments is intended to provide illustration and description, but is not intended to be exhaustive or to limit the invention to the precise form disclosed. Modifications and variations are possible in light of the above teachings or may be acquired from practice of the invention.

No element, act, or instruction used herein should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A system comprising:
a plurality of sensor devices contained in a respective plurality of wells, the wells defined by a well plate having a hollow cylinder and a corresponding sensor device of the plurality of sensor devices for each well, each hollow cylinder closed by a seal at one end, the sensor device and a compressive connector defined by a compressibly conductive ring disposed between the sensor device and a printed circuit board (PCB) coupled against the well plate, each sensor device having a resonant frequency and a motional resistance that varies based on a visco-elastic mass of biological cells contained in a corresponding well, the compressibly conductive ring for transporting signals indicative of the resonant frequency between the PCB and the sensor device: and an electronic circuit on the PCB, including processor coupled to the PCB, the processor and PCB programmed to:
generate a reference signal to identify, for each sensor device, the resonant frequency and the motional resistance of the sensor device based on the visco-elastic mass of biological cells contained in the corresponding well, the sensor device responsive to the visco-elastic mass deposited on the sensor device for generating an output signal indicative of the elastic mass; and
apply the reference signal to the sensor device via the compressibly conductive ring, the sensor device outputting an output signal based on the reference signal; and
receive, from each respective sensor device, the output signal indicative of
the visco-elastic mass, the output signal passed to the processor via the compressibly
conductive ring, the processor and PCB further programmed to:
identify a difference in phase between the reference signal and the output signal; and
identify the resonant frequency of the sensor device based on the identified difference in phase.

2. The system of claim 1, wherein a sensor device includes a quartz crystal.

3. The system of claim 1, wherein the processor and PCB are programmed to: generate a tuning word based on the identified difference in phase; and implement a numerically controlled oscillator (NCO) for generating the reference signal based on a value of the tuning word, wherein a frequency of the reference signal is determined by the value of the tuning word.

4. The system of claim 1, wherein the processor and PCB are further programmed to identify a phase difference between the reference signal and the output signal by: implementing an impedance divider, the impedance divider having: a measured portion for producing a signal that represents a phase of the output signal, and a reference portion, for producing a signal that represents a phase of the reference signal; and comparing the signal produced by the measured portion with the signal produced by the reference portion to identify the difference in phase between the reference signal and the output signal.

5. The system of claim 1, wherein the processor and PCB are programmed to: identify a difference in amplitude between the reference signal and the output signal; and identify the motional resistance of the sensor device based on the identified difference in amplitude.

6. The system of claim 5, wherein the processor and PCB are programmed to generating a reference signal by: generating an amplitude word based on the identified difference in amplitude; and implementing an NCO for generating the reference signal based on a value of the amplitude word, wherein an amplitude of the reference signal is determined by the value of the amplitude word.

7. The system of claim 5, wherein the processor and PCB are programmed to identify a difference in amplitude between the reference signal and the output signal by— implementing an impedance divider, the impedance divider having: a measured portion for producing a signal that represents an amplitude of the output signal, and a reference portion, for producing a signal that represents an amplitude of the reference signal; and comparing the signal produced by the measured portion with the signal produced by the reference portion to identify the difference in amplitude between the reference signal and the output signal.

8. The system of claim 1, wherein the quality of biological cells includes at least one of surface coupled mass, density, viscosity, or viscoelasticity of the biological cells.

9. The system of claim 1, wherein a first well, in the plurality of wells, is used as a control well for an experiment and a second well, in the plurality of wells, is used as an experimental well for the experiment, and
wherein the first well contains a first sensor device and the second well contains a second sensor device, and
wherein a resonant frequency and motional resistance of the first sensor device is identified while a resonant frequency and motional resistance of the second sensor device is identified.

10. An apparatus comprising: a well plate containing a plurality of wells, the plurality of wells defined by a hollow cylinder in the well plate for each well of the plurality of wells, the hollow cylinder closed at one end by a seal and a flexible electrically conductive connector against a printed circuit board (PCB); for each well: a respective sensor device contained in the well, each respective sensor device disposed between the seal and the flexible electrically conductive connector to transmit an electrical signal that represents a resonant frequency and motional resistance of the sensor device based on a visco-elastic mass of biological cells contained in the corresponding well, the flexible electrically conductive connector for transporting the electrical signals indicative of the resonant frequency between the PCB and the sensor device; and the flexible electrically conductive connector electrically connected to the sensor device, the electrically conductive connector coupled for transferring the electrical signal from the sensor device of the corresponding well to the PCB; and the PCB and processor programmed to: transmit a reference signal based on the visco-elastic mass of biological cells contained in the corresponding well; conduct the reference signal to the sensor device; acquire an output signal transferred from the respective sensor device of the plurality of wells via corresponding flexible electrically conductive connectors, and provide the output signal to a computer system and processor coupled to the PCB.

11. The apparatus of claim 10, further comprising:
a guide for aligning the flexible electrically conductive connectors corresponding to each well with corresponding electrical connections contained on the printed circuit board.

12. The apparatus of claim 11, further comprising:
a seal between the well plate and the guide.

13. The apparatus of claim 10, further comprising:
a stiffener for supporting the printed circuit board.

14. The apparatus of claim 10, wherein the flexible electrically conductive connectors include an elastomer and an electrical conductive component that enables the flexible electrically conductive connectors to conduct electrical signals when compressed.

15. The apparatus of claim 10, wherein the sensor device includes a quartz crystal.

16. The apparatus of claim 10, wherein the flexible electrically conductive connector is shaped to form a cylinder, and
wherein a first end of the cylinder is connected to the sensor device and a second end of the cylinder is connected to the PCB.

17. The system of claim 1 wherein the electronic circuit includes logic for performing rising edge sampling for identifying the resonant frequency.

18. The system of claim 1, wherein the electronic circuit includes an oscillation circuit for driving the sensor at an oscillation frequency.

* * * * *

UNITED STATES PATENT AND TRADEMARK OFFICE
CERTIFICATE OF CORRECTION

PATENT NO. : 11,150,236 B2
APPLICATION NO. : 15/436136
DATED : October 19, 2021
INVENTOR(S) : Dewilde et al.

It is certified that error appears in the above-identified patent and that said Letters Patent is hereby corrected as shown below:

In the Claims

Column 17, Line 67, after the word "device", delete ":", add --;--

Column 18, Line 1, after the word "including", add --a--

Column 18, Line 51, delete "generating", add --generate--

Column 18, Line 59, after the word "by", delete "--", add --:--

Signed and Sealed this
Twenty-fifth Day of January, 2022

Drew Hirshfeld
*Performing the Functions and Duties of the
Under Secretary of Commerce for Intellectual Property and
Director of the United States Patent and Trademark Office*